(12) United States Patent
Beger et al.

(10) Patent No.: US 9,351,781 B2
(45) Date of Patent: May 31, 2016

(54) SURGICAL PROCEDURE FOR EXPANDING A VERTEBRAL CANAL

(75) Inventors: Jens Beger, Tuttlingen (DE); Ralph Linke, Steisslingen (DE); Petr Suchomel, Liberec (CZ); Susanne Klingseis, Biberach (DE)

(73) Assignee: Aesculap AG, Tuttlingen (DE)

( * ) Notice: Subject to any disclaimer, the term of this patent is extended or adjusted under 35 U.S.C. 154(b) by 1067 days.

(21) Appl. No.: 13/438,901

(22) Filed: Apr. 4, 2012

(65) Prior Publication Data

US 2012/0265302 A1    Oct. 18, 2012

Related U.S. Application Data

(60) Provisional application No. 61/474,393, filed on Apr. 12, 2011.

(51) Int. Cl.
*A61F 2/44* (2006.01)
*A61B 17/88* (2006.01)
(Continued)

(52) U.S. Cl.
CPC ............ *A61B 17/8866* (2013.01); *A61B 17/025* (2013.01); *A61B 17/0206* (2013.01); *A61B 17/1757* (2013.01); *A61B 17/7071* (2013.01); *A61F 2/44* (2013.01); *A61B 17/0293* (2013.01); *A61B 17/683* (2013.01); *A61B 17/86* (2013.01); *A61B 17/8625* (2013.01); *A61B 2017/0256* (2013.01); *A61B 2019/461* (2013.01); *A61B 2019/464* (2013.01); *A61F 2/4611* (2013.01); *A61F 2002/3093* (2013.01); *A61F 2002/30158* (2013.01); *A61F 2002/30172* (2013.01); *A61F 2002/30232* (2013.01); *A61F 2002/30266* (2013.01); *A61F 2002/30563* (2013.01); *A61F 2002/30566* (2013.01); *A61F 2002/30571* (2013.01); *A61F 2002/30576* (2013.01);
(Continued)

(58) Field of Classification Search
CPC ........... A61B 17/7071; A61B 17/7062; A61B 17/1732; A61B 2017/7073; A61B 2017/0256
See application file for complete search history.

(56) References Cited

U.S. PATENT DOCUMENTS 5,980,572 A    11/1999  Kim et al.
6,080,157 A    6/2000   Cathro et al.
(Continued)

FOREIGN PATENT DOCUMENTS

DE           602 12 648      6/2007
DE       20 2010 000 341     6/2010
(Continued)

OTHER PUBLICATIONS

F. Meyer et al., "Die degenerative zervikale Spinalkanalstenose", Deutsches Aerzteblatt, Jg. 105, Heft 20, pp. 366-372, May 16, 2008. An English language translation is attached.
(Continued)

*Primary Examiner* — Mary Hoffman
(74) *Attorney, Agent, or Firm* — Lipsitz & McAllister, LLC

(57) ABSTRACT

To provide a method with which expansion of the vertebral canal of vertebrae is possible with less stress for the patient than with the surgical methods used to date, it is proposed that herein the vertebral arch be split and an incision gap thereby be formed, and the incision gap bounded by opposed incision surfaces be expanded to a prescribed gap width and the bone substance of the resulting vertebral arch sections thereby be elastically/plastically deformed.

25 Claims, 27 Drawing Sheets

(51) Int. Cl.
  *A61B 17/02* (2006.01)
  *A61B 17/17* (2006.01)
  *A61B 17/70* (2006.01)
  A61B 17/68 (2006.01)
  A61B 17/86 (2006.01)
  A61B 19/00 (2006.01)
  A61F 2/46 (2006.01)
  A61F 2/30 (2006.01)

(52) U.S. Cl.
  CPC .......... *A61F2002/30777* (2013.01); *A61F 2002/30787* (2013.01); *A61F 2002/30794* (2013.01); *A61F 2002/30848* (2013.01); *A61F 2002/30883* (2013.01)

(56) References Cited

U.S. PATENT DOCUMENTS

| | | |
|---|---|---|
| 6,572,617 B1 | 6/2003 | Senegas |
| 6,635,087 B2 | 10/2003 | Angelucci et al. |
| 6,652,593 B2 | 11/2003 | Boyer, II et al. |
| 6,776,800 B2 | 8/2004 | Boyer, II et al. |
| 6,855,169 B2 | 2/2005 | Boyer, II et al. |
| 6,997,953 B2 | 2/2006 | Chung et al. |
| 7,264,620 B2 | 9/2007 | Taylor |
| 7,608,113 B2 | 10/2009 | Boyer, II et al. |
| 7,753,963 B2 | 7/2010 | Boyer, II et al. |
| 8,105,366 B2 | 1/2012 | Null et al. |
| 8,323,292 B2 | 12/2012 | Dudasik et al. |
| 2002/0120335 A1 | 8/2002 | Angelucci et al. |
| 2002/0120338 A1 | 8/2002 | Boyer, II et al. |
| 2002/0120346 A1 | 8/2002 | Boyer, II et al. |
| 2002/0120347 A1 | 8/2002 | Boyer, II et al. |
| 2003/0045935 A1 | 3/2003 | Angelucci et al. |
| 2003/0045936 A1 | 3/2003 | Angelucci et al. |
| 2003/0050700 A1* | 3/2003 | Kihara ............... 623/17.11 |
| 2003/0125738 A1 | 7/2003 | Khanna |
| 2003/0125740 A1 | 7/2003 | Khanna |
| 2004/0030388 A1 | 2/2004 | Null et al. |
| 2004/0107003 A1 | 6/2004 | Boyer, II et al. |
| 2004/0153155 A1 | 8/2004 | Chung et al. |
| 2004/0210222 A1 | 10/2004 | Angelucci et al. |
| 2004/0254428 A1 | 12/2004 | Ritland |
| 2005/0107877 A1 | 5/2005 | Blain |
| 2005/0131412 A1 | 6/2005 | Olevsky et al. |
| 2005/0131548 A1 | 6/2005 | Boyer, II et al. |
| 2005/0251138 A1 | 11/2005 | Boris et al. |
| 2005/0273100 A1 | 12/2005 | Taylor |
| 2006/0074431 A1 | 4/2006 | Sutton et al. |
| 2008/0009865 A1 | 1/2008 | Taylor |
| 2008/0215096 A1 | 9/2008 | Nash et al. |
| 2009/0005882 A1 | 1/2009 | Boyer, III et al. |
| 2009/0048675 A1 | 2/2009 | Bhatnagar et al. |
| 2009/0177285 A1 | 7/2009 | Frey et al. |
| 2009/0198240 A1 | 8/2009 | Kaufman |
| 2009/0198278 A1 | 8/2009 | Shibata et al. |
| 2009/0210012 A1 | 8/2009 | Null et al. |
| 2009/0259107 A1 | 10/2009 | Crenshaw et al. |
| 2010/0057127 A1 | 3/2010 | McGuire et al. |
| 2010/0063590 A1 | 3/2010 | Cannestra |
| 2010/0069960 A1 | 3/2010 | Chaput |
| 2010/0114100 A1 | 5/2010 | Mehdizade |
| 2010/0152745 A1 | 6/2010 | Dudasik et al. |
| 2010/0152854 A1 | 6/2010 | Slivka et al. |
| 2010/0161056 A1 | 6/2010 | Voellmicke et al. |
| 2010/0185239 A1 | 7/2010 | Patel et al. |
| 2010/0185240 A1 | 7/2010 | Mangione et al. |
| 2010/0241165 A1 | 9/2010 | Konieczynski et al. |
| 2010/0241230 A1 | 9/2010 | Mazzuca et al. |
| 2011/0046680 A1 | 2/2011 | Khanna |
| 2011/0106083 A1 | 5/2011 | Voellmicke et al. |
| 2011/0106087 A1 | 5/2011 | Gamache |
| 2011/0106168 A1 | 5/2011 | Bucci et al. |
| 2011/0106169 A1 | 5/2011 | Zalenski et al. |
| 2011/0166601 A1 | 7/2011 | Cain |
| 2012/0078304 A1* | 3/2012 | Jensen et al. ............... 606/251 |
| 2012/0165942 A1* | 6/2012 | Khanna ............... 623/17.16 |
| 2014/0142699 A1* | 5/2014 | Beger et al. ............... 623/17.11 |

FOREIGN PATENT DOCUMENTS

| | | |
|---|---|---|
| EP | 2 196 160 | 6/2010 |
| EP | 2 091 446 | 10/2011 |
| JP | 2000139970 | 5/2000 |
| JP | 2001149392 | 6/2001 |
| JP | 2001170092 | 6/2001 |
| WO | WO 03/020143 | 3/2003 |
| WO | WO 2008/139260 | 11/2008 |
| WO | WO 2009/025884 | 2/2009 |
| WO | WO 2010/033567 | 3/2010 |
| WO | WO 2010/107546 | 9/2010 |
| WO | WO 2010/144636 | 12/2010 |
| WO | WO 2011/053523 | 5/2011 |

OTHER PUBLICATIONS

X. Wang, et al., "Prediction of Spinal Canal Expansion Following Cervical Laminoplasty: A Computer-Simulated comparison Between Single and Double-Door Techniques", SPINE, vol. 31, No. 24, pp. 2863-2870, 2006.

M. Wang, et al., "Minimally Invasive Cervical Expansile Laminoplasty: An Initial Cadaveric Study", Neurosurgery, vol. 52, No. 2, pp. 370-373, Feb. 2003.

D. Benglis, et al., "Clinical Feasibility of Minimally Invasive Cervical Laminoplasty", Neurosurg Focus, vol. 25, pp. 1-4, Aug. 2008.

* cited by examiner

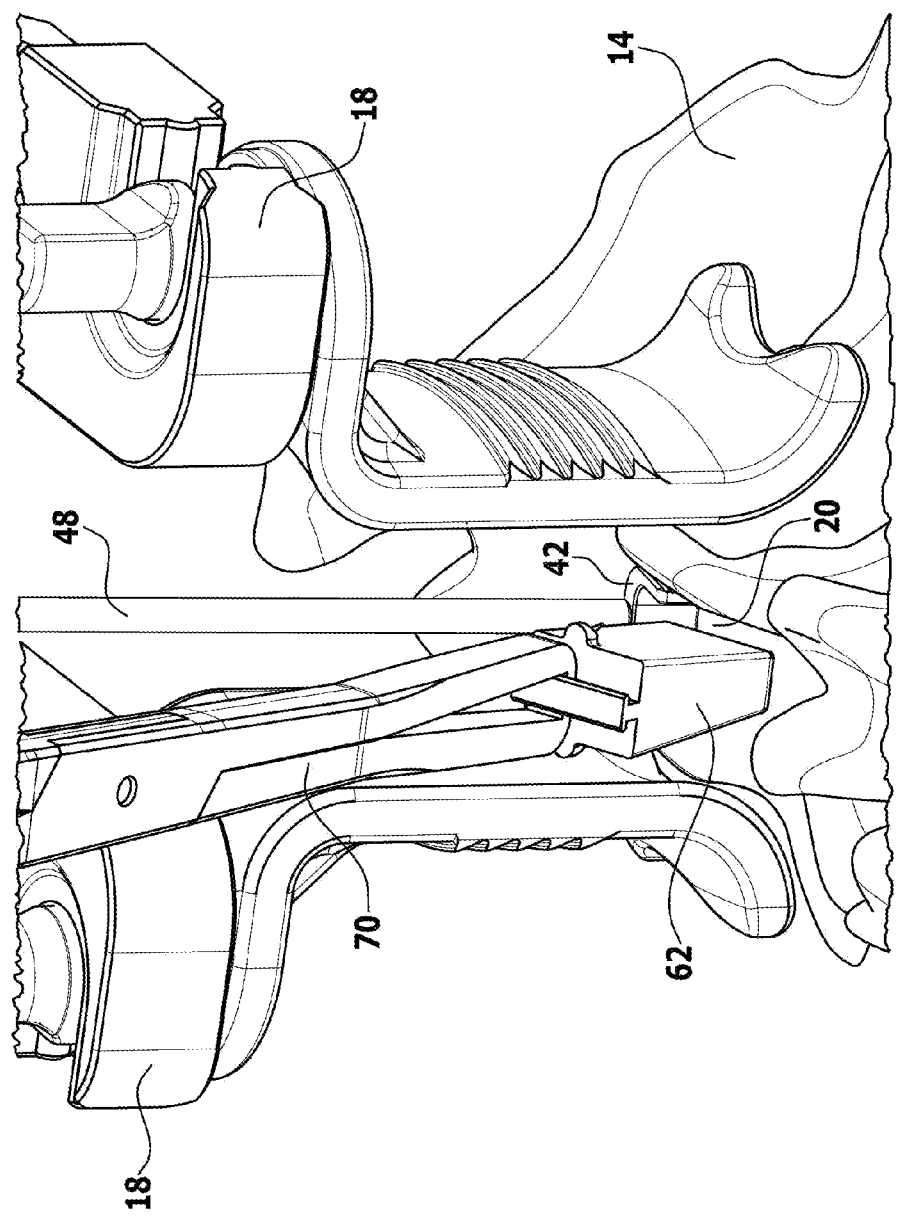

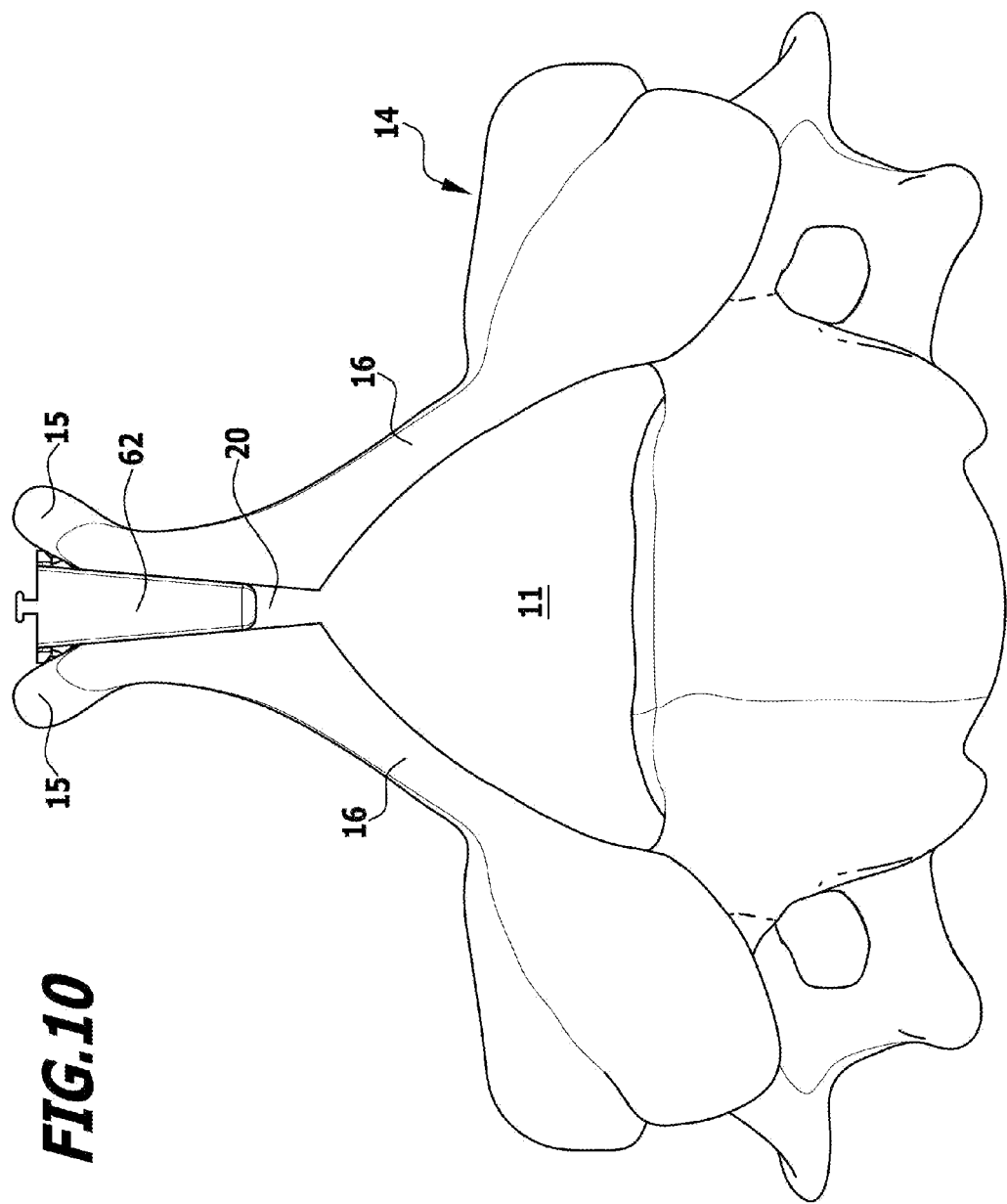

FIG.12
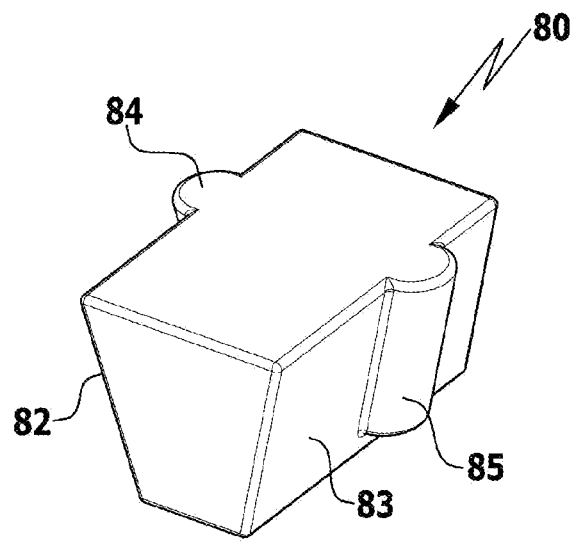
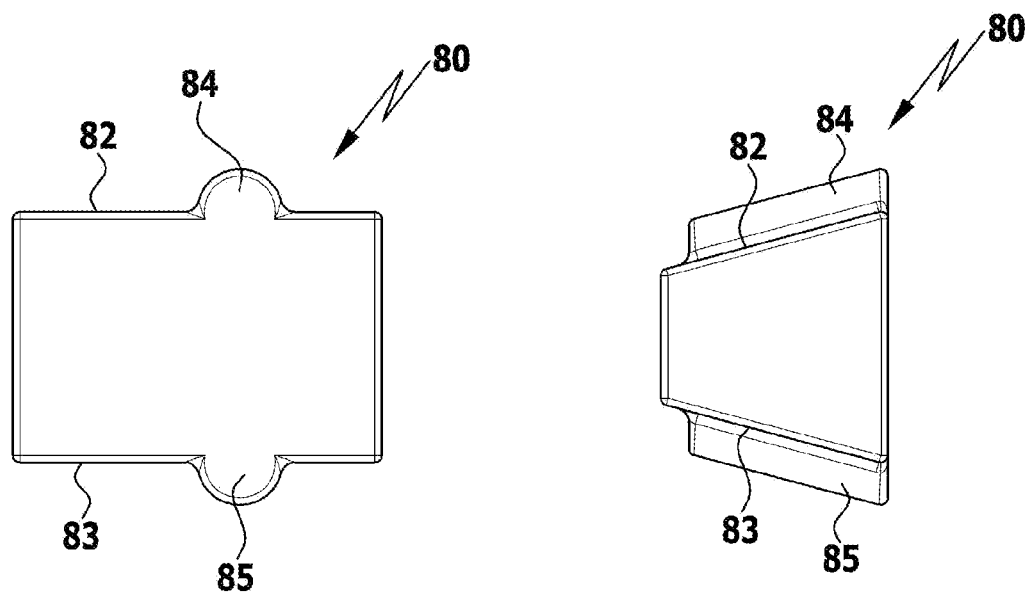

FIG.13
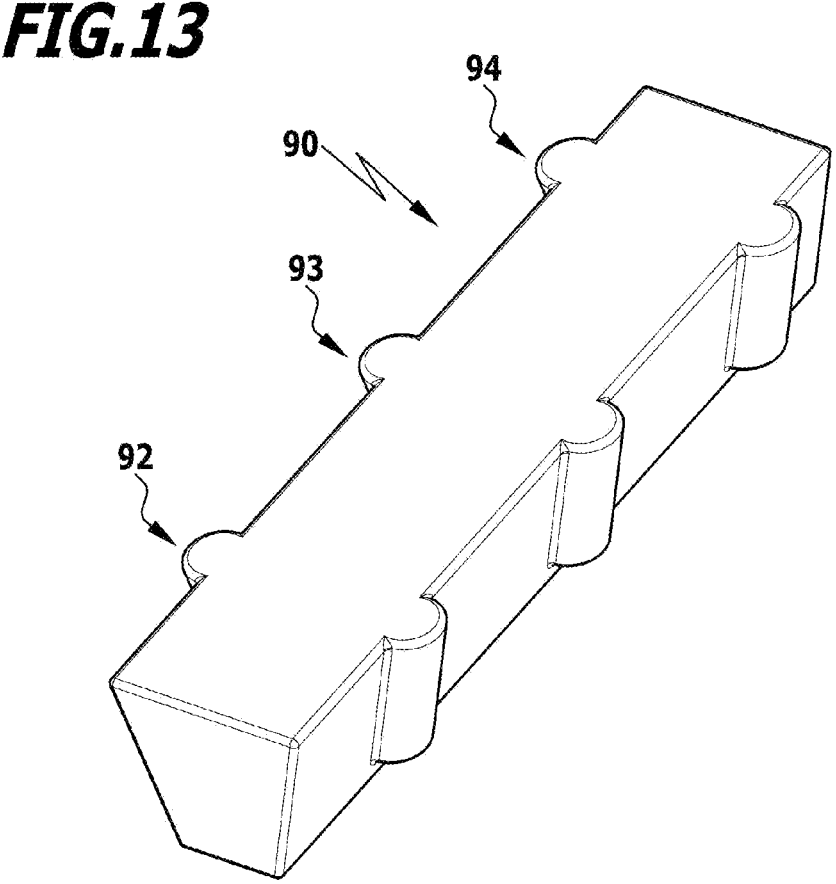
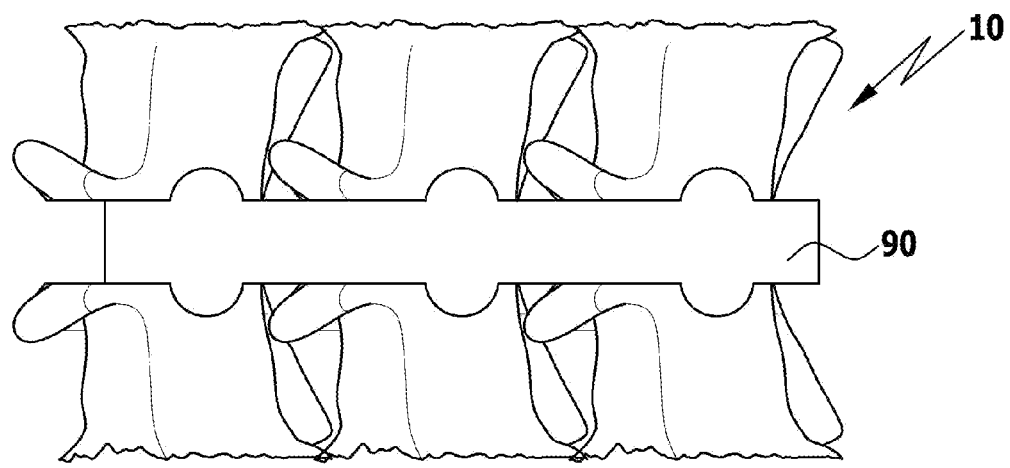

SURGICAL PROCEDURE FOR EXPANDING A VERTEBRAL CANAL

This application claims the benefit of commonly-owned U.S. provisional application No. 61/474,393 filed on Apr. 12, 2011, which is incorporated herein and made a part hereof by reference.

BACKGROUND OF THE INVENTION

The invention relates to a surgical method for expanding a vertebral canal of a vertebra of the spine, also called laminoplasty.

The vertebral canals of the vertebrae of the spine form the so-called canalis vertebralis or spinal canal in which the spinal cord, enclosed by the spinal meninx, is located.

The spinal cord as part of the central nervous system may be prevented from functioning properly if, for example, with the occurrence of spinal canal stenosis, pressure is exerted on the spinal cord. This may have several causes, for example, the existence of spondylosis or ossification of the posterior longitudinal ligament.

This may be remedied by enlargement of the vertebral canal of the vertebra or vertebrae of the spine that is or are affected so that the spinal cord has more space available and can therefore evade the pressure.

An overview of the therapeutic options commonly used to date can be found, for example, in F. Meyer et al., Deutsches Ärzteblatt, year 105, issue 20, pages 366 to 372. In addition to the ventral methods, various dorsal methods, namely laminectomy with and without fusion and laminoplasty, are used. Ventral methods may also be used in combination with dorsal methods.

Of the various dorsal methods, laminoplasty works with the least surgical interventions in the bone substance.

To date, various laminoplasty operating techniques have been proposed. The two most important of these are described in the literature as so-called single-door or double-door techniques. An overview of these and an assessment of the effects to be expected with regard to pressure relief and expansion of the spinal canal is, for example, to be found in the publication by Wang, Xiang-Yang et al. in SPINE, Vol. 31, No. 24, 2006, pages 2863 to 2870.

In the so-called single-door technique, also called open-door technique, the lamina is split on one side of the vertebra with an incision gap, whereas on the other side of the lamina a groove is made without splitting the vertebral arch.

The area of the vertebral arch with the groove acts like a hinge during the subsequent opening of the vertebral canal and allows the vertebral arch to be opened, which involves fracture of the bone substance. The vertebral arch remains joined to the vertebral body by the periosteum and the collagenous fibers of the bone substance.

In the so-called double-door technique, the spinous process of a vertebra is split or completely removed and a groove is made in the lamina on both sides of the spinous process, with the areas of the vertebral arch containing the grooves again acting as hinges. The vertebral canal is now opened by swinging apart the two vertebral arch sections with the associated spinous process parts, if still existing, and the bone substance in the area of the hinges likewise fractures. Here, too, the vertebral arch sections remain joined to the vertebral body by the periosteum and the collagenous fibers of the bone substance.

With both techniques, the vertebral canal of the vertebrae is fixed in the opened state by implants. In addition to the body's own bone chip, an hydroxyapatite spacer or the like is used as implant material.

In spite of the reduced surgical intervention in the bone substance in comparison with other dorsal methods, a significantly increased rate of subsequent neck pain is still regarded as a disadvantage of laminoplasty, as is restricted mobility of the cervical spine, which is often observed.

SUMMARY OF THE INVENTION

The object of the invention is to provide a method enabling expansion of the vertebral canal of vertebrae with less stress for the patient.

This object is accomplished by a surgical method in accordance with the various embodiments of the present invention.

A major difference of the method in accordance with the invention over the previously discussed single-door and double-door techniques of laminoplasty lies in the fact that, firstly, only a single splitting incision has to be made on the vertebral arch and a detachment of muscles from the spine is avoided to a large extent or is essentially even avoided entirely. Furthermore, there is no occurrence of fracture of the bone substance of the lamina as expansion of the vertebral arch is achieved by elastic/plastic deformation thereof.

Owing to the inherent viscoelastic properties of the bone substance, the elastic/plastic deformation occurs additionally with the method in accordance with the invention, but without this leading to fracture of the bone substance. It is preferable for the expansion not to be forced abruptly, but to be performed gradually, so that the viscoelastic properties of the bone substance can come into play. This can happen continuously or in small steps of, for example, about 0.5 mm to about 3 mm each. Typically, a gap expansion of about 15 mm within about 10 sec to about 5 min, in particular, within about 30 sec to about 3 min, further preferred within about 1 min to about 2 min, can in this way be achieved for the C6 vertebra. To put it another way, the spacing of the incision surfaces of the incision gap is enlarged by 5 mm within a time frame of about 3 sec to about 100 sec, in particular, about 10 sec to about 60 sec, even further preferred within about 20 sec to about 40 sec.

This elastic/plastic deformation for expansion of the incision gap with minimized risk of fracture of the bone substance is achieved, in particular, by limiting the forces used for the expanding to about 500 N or less, in particular, about 300 N or less.

This counteracts the problem of the laminoplasty techniques used to date, which first necessitate extensive surgical interventions on the muscles extending parallel to the spine, which also mean considerable stress for the patient in the postoperative phase.

The method in accordance with the invention involves, in particular, considerably less surgical intervention than the prior art and no lateral detachment of muscles from the spine.

Furthermore, minimal surgical interventions in the bone substance are sufficient, and further damage to the bone substance of the vertebral arch is avoided.

In particular, when the splitting incision is made in the area of the spinous process, the location at the vertebra is very easy to access, and the muscles parallel to the spine can be left substantially untouched.

The incision gap may be produced with very different tools. For example, the incision gap may be made with an ultrasonic osteotome, with incision gaps of about 1 mm or less resulting.

Other techniques use high-speed drills or burrs (craniotome) with which somewhat wider incision gaps are obtained, for example, ranging from about 2 mm to about 3 mm.

Another technique uses the so-called T-saw or Gigli saw, but here there is a certain difficulty in initially introducing the saw without injuring the spinal meninx. The same applies to use of the craniotome.

Whereas with the ultrasonic osteotome, it is readily possible to make the incision gap without damaging the spinal meninx, it is recommended, when drills are used, that the last part of the incision be carried out with a so-called Kerrison punch. This may also be used in combination with the ultrasonic osteotome if the depth of the incision gap is very large as, for example, in the case of the C6 or C7 vertebrae.

When using the craniotome, a stop, which during the movement of the burr acts as a guide on the spinal canal side along the bone, is used in order to protect the dura.

The ultrasonic osteotome or the high-speed drill are, therefore, used in combination with a Kerrison punch in preferred methods.

Surprisingly, in spite of the minimal surgical interventions required in accordance with the invention, it is possible with the laminoplasty technique in accordance with the invention to obtain access to the spinal canal and expansion thereof, which are comparable to the conventional single-door and double-door techniques as regards the clinical results to be expected.

Also, with the method in accordance with the invention, the advantage is gained that the bone material outside the area comprising the incision gap is left untouched and is only elastically or plastically deformed without fracturing the bone material, whereas, conventionally, permanent deformations are produced with fractures of the bone material in the area of the weakenings of the lamina for the formation of hinge areas. Therefore, the healing phase following a surgical intervention in accordance with the invention is typically considerably shorter and involves significantly less stress for the patient.

Special distraction instruments, in particular, distraction forceps, are preferably used for elastic/plastic expansion of the incision gap. It is preferable for these to be equipped with guide elements for safe placement of an implant, and it is also preferable for them to comprise a measuring unit for displaying the incision gap expansion achieved.

When introducing the distraction instrument, the incision gap may be slightly widened with a thin blade or a raspatory.

In view of the further steps such as, for example, insertion of a spacer or also the implant, it is preferable to use a distraction instrument, the points of which are angled. The angled points can be pushed under the lamina, i.e., they bear against the spinal canal side of the lamina and thereby ensure a secure seating during expansion of the incision gap.

The forces required for expanding the incision gap are typically about 70 N to about 200 N, in particular, about 80 N to about 150 N for expansion of the gap by about 5 mm to about 12 mm, determined, in each case, at the end of the incision gap on the spinal canal side.

In the majority of cases, the elastic/plastic expansion is achieved without fracturing the bone material. If a fracture was observed during expansion by up to about 10 mm, it then related to the fracture in the area of the spinous process.

The distraction forces are, therefore, preferably introduced as close as possible to or better in the area of the vertebral arch and not in the area of the spinous process.

If required, prior to insertion of an implant, it is also possible to temporarily insert into the expanded incision gap a spacer, which is preferably of U-shaped configuration and maintains free access to the spinal canal. Here, too, it is preferable to insert the spacer into the incision gap to such a depth that it comes to rest in the area of the vertebral arch and not or not exclusively in the area of the spinous process. The orientation of the U-shape in relation to the vertebra is cranial/caudal in this case.

The spacer is often already held adequately by the elastically/plastically spread vertebral arches in the incision gap. If unintentional movement of the spacer is to be avoided, it can be fixed to the patient's skin or to a retractor or the like keeping the surgical wound open.

The inserted U-shaped spacer allows a substantially unobstructed view of and access to the spinal cord and the spinal meninx.

The expansion, in accordance with the invention, of the vertebral canal of a vertebra also creates access to cranially or caudally adjacent vertebral canals to such an extent that a decompression of the spinal cord is achievable there with the so-called undercutting technique.

In this connection, angled Kerrison punches which enable a particularly good view of the site of the operation are preferred.

It is, for example, thus possible by means of the inventive expansion of the vertebral canals of the C4 and C6 vertebrae to achieve a decompression in the entire section of the cervical spine from C3 to C7.

The two incision surfaces defining the incision gap in the vertebral body are preferably expanded to a spacing of about 5 mm to about 15 mm, measured at the end of the incision gap on the spinal canal side.

The incision surfaces of the incision gap are fixed in the expanded position by instruments or implants in a way which is similar to how this is also possible in connection with the prior art operating method.

The implants used in accordance with the invention may be of solid or hollow-body configuration. The hollow-body implants may, in particular, have different bore holes or through-openings.

The material from which the implant is made is preferably a biocompatible plastic material, in particular, PEEK, or titanium or a titanium alloy. The body's own bone chips are also suitable.

Implants made of plastic, in particular, PEEK, are preferably provided with an osteointegrative coating on the surfaces contacting the bone material. This coating is preferably applied as microporous pure titanium coating using the VPS process (Plasmapore technique) or as hydroxyapatite coating.

The plastic implants are preferred over titanium implants as they are compatible with the MRT procedure. This is of particular importance for the postoperative phase. MRT compatibility also exists with the osteointegratively coated plastic implants described above.

Implants made of titanium preferably have a porous structure or a grid structure.

The implant will preferably have a wedge shape, so that as full surface contact as possible of the surfaces of the wedge-shaped body at the incision surfaces of the expanded incision gap is achievable, the incision surfaces initially being arranged in parallel after formation of the incision gap, but being inclined to each other in the shape of a wedge after the elastic expansion of the incision gap.

The method in accordance with the invention can be performed substantially without detachment of muscles from the vertebral arch, particularly if the incision gap is made in the area of the spinous process.

The method in accordance with the invention is appropriate particularly when a surgical intervention is performed on the grounds of diagnosis of cervical spondylotic myelopathy (CSM) or ossification of the posterior longitudinal ligament (OPLL).

If, in exceptional cases, fracturing of the bone substance occurs with the inventive elastic/plastic expansion of the vertebral arch, typically, no splintering thereof is observed, so that the operation can be continued in the conventional manner, for example, by laminectomy.

Advantageously, in accordance with the inventive method, recesses are formed in the incision surfaces of the incision gap. These may have a number of functions:

Firstly, the recesses of the incision surfaces may receive corresponding projections which can be formed on the contacting surfaces of the implant bodies and thus secure the implant body inserted in the incision gap in its position.

It is preferable for the recesses to be formed as grooves, which preferably extend parallel to the longitudinal axis of the spinous processes. For example, the grooves can be made as bore hole in the bone material, optionally, before the incision gap is created. In this case, the incision gap is then placed centrally in relation to the bore hole which already exists.

It is also possible for the grooves to be made in the incision surfaces after expansion of the incision gap. In this case, it is preferable to first insert in the expanded incision gap a spacer which may then optionally also be configured and used as drilling gauge for making the grooves.

In general, the grooves may be made by drilling or punching.

The grooves enlarge the cross section of access to the spinal canal and thus facilitate insertion of instruments into the spinal canal.

A further aspect consists in guiding the implant bodies during insertion into the incision gap, with the projections of the contacting surfaces of the implant bodies slidingly engaging the grooves of the incision surfaces.

The grooves may also act as positioning aid for the distraction instruments. If the implant bodies are to be inserted into the incision gap immediately after sufficient distraction of the vertebral arch sections, then the distraction instrument, partly accommodated by the grooves, can remain in the incision gap and hold it in its expanded position, while implant bodies, preferably with corresponding grooves on their contacting surfaces, are inserted into the incision gap, thereby being guided by the distraction instrument.

The height of the implant preferably matches the depth of the incision gap and thus creates a maximum surface for the implant to bear on the incision surfaces and hence low surface pressure on the part of the bone substance. This is also of importance in view of the fact that the implants remain permanently in the patients' body.

In accordance with the invention, the implants, with their implant body inserted in the incision gap, may be fixed in various ways to the bone material.

The previously mentioned formation of recesses in the incision surfaces and of projections in the contacting surfaces of the implant bodies may be used to create a positive locking between the incision gap or the bone substance of the vertebra and the implant.

The forces acting on the implant body owing to the elastic/plastic expansion of the vertebral arch also lead to a certain initial force locking. In the course of time, this decreases on account of the viscoelastic properties of the bone substance.

Alternatively or additionally, provision may be made to anchor the implant body with additional fastening means to the bone substance.

For example, the implant body may have one or more bore holes, through which the implant body may be fixed by means of pins or screws which engage the bone substance.

A further alternative consists in fixing the implant body with suture material or wires to the vertebral arch. Metal or plastic bridges which engage over the implant body can also be fixed on either side or the incision gap to the bone substance in order to hold and secure the implant body in the incision gap.

Preferred implant bodies comprise a locking element, preferably integrated in the body, which can be activated after positioning of the implant body in the incision gap.

Bone screws whose flanks are arranged within the implant body in a rotational position and upon rotation through about 90° extend beyond the contacting surfaces of the implant body and cut into the surrounding bone substance may, for example, serve as locking elements.

A further alternative for fixing the implant body in the incision gap consists in establishing a substance-to-substance bond between the implant body and the surrounding bone substance. Plastifiable or curable materials or so-called hot-melt adhesives, which can be activated by ultrasound, heat, HF or also UV light, are suitable for the substance-to-substance bond.

In accordance with a variant of the method in accordance with the invention, after an initial expansion of the incision gap, an intracanal weakening of the lamina is carried out to reduce the resistance of the bone substance to the elastic/plastic deformation. Even if, in this case, the lamina is partially removed in areas remote from the spinous process, this is again done, in accordance with the invention, without detaching the muscles from the spine over a large area.

If an implant with projections is used, then the projections are arranged on the wedge surfaces of the wedge-shaped implant.

The recesses on the incision surfaces of the incision gap are preferably formed as grooves, and semi-cylindrical grooves are particularly recommended.

The projections and recesses, seen in the sagittal direction, are preferably arranged eccentrically, so that, in the inserted state of the implant, they are arranged substantially outside of the area of the incision gap bounded by the spinous processes.

The projections on sides of the implant are then preferably of semi-cylindrical configuration to match the shapes of the grooves, so that a contacting of bone material and implant over as large an area as possible is also ensured in the area of the projections and recesses.

The grooves are preferably arranged so as to extend ventrally/dorsally or, in other words, essentially in the radial direction of the vertebrae.

The grooves and the corresponding projections then secure the implants against unintentional displacement in the axial direction of the vertebrae.

These and further advantages of the invention will be explained in greater detail hereinbelow with reference to the drawings.

BRIEF DESCRIPTION OF THE DRAWINGS

The present invention will hereinafter be described in conjunction with the appended drawing figures, wherein like reference numerals denote like elements.

FIG. 9 shows insertion of an implant in accordance with the invention into the incision gap which is held open by a spacer;

FIG. 10 shows the implant inserted in accordance with the invention in the incision gap of the vertebra;

FIG. 12 shows basic shape of a second embodiment of the implant in accordance with the invention in a perspective view, a plan view and a side view;

FIG. 13 shows basic shape of a first embodiment of a multiple implant in a perspective representation and in a plan view in the implanted state;

DETAILED DESCRIPTION

Figure 1A:
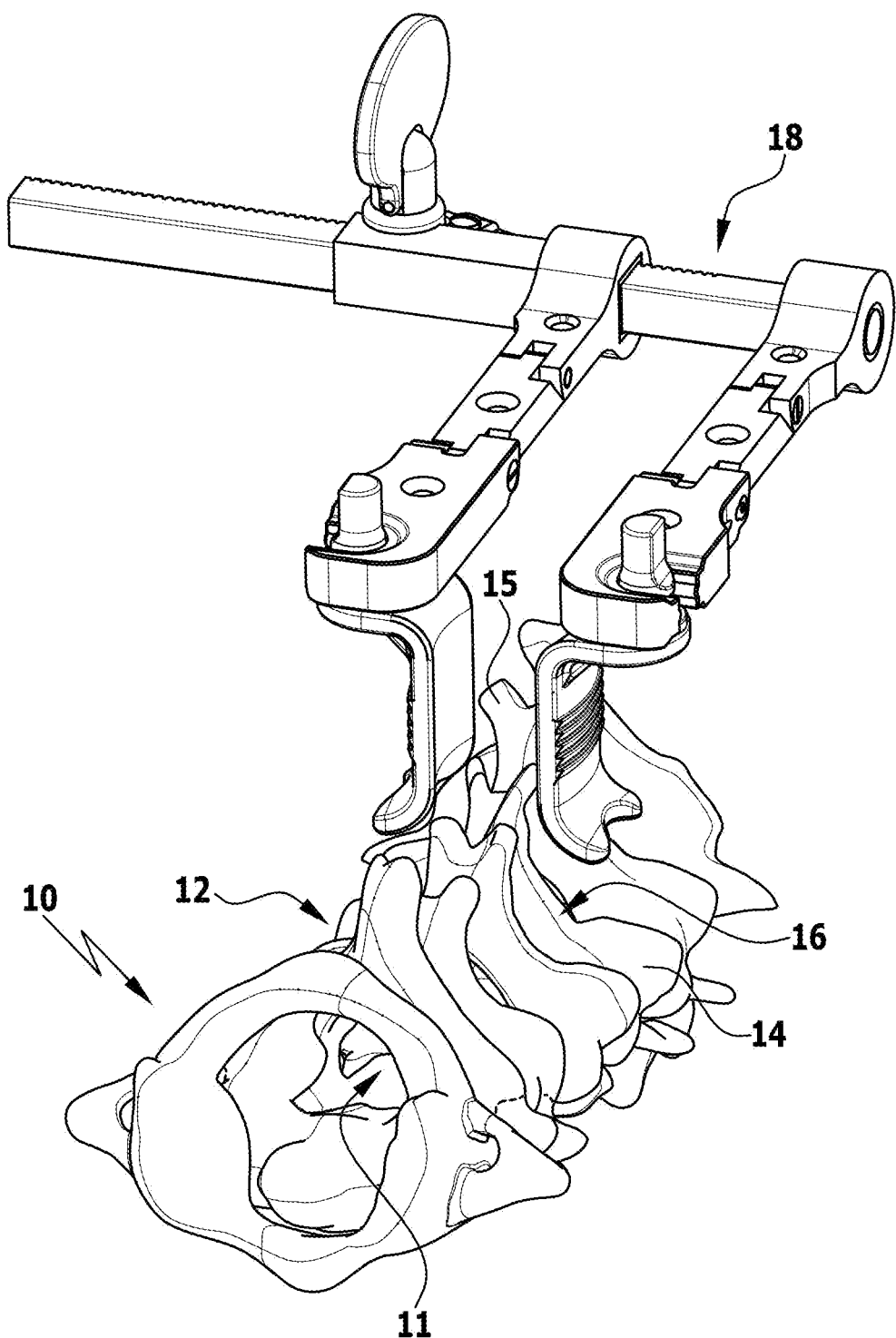
FIGS. 1A and 1B show part of the cervical spine with a cervical vertebra provided in accordance with the invention with an incision gap in a perspective view and a plan view, respectively.

FIG. 1A shows in schematic representation the section C1 to C7 of a cervical spine 10 with a spinal canal 11 and a retractor 18 positioned over a vertebral arch of a vertebra 14. The retractor 18 holds back the surrounding tissue (omitted in FIG. 1 for reasons of clarity), so that the area of the vertebra 14 remains dorsally accessible.

In accordance with the invention, access to the vertebra 14 and its vertebral arch 12 is possible without detaching muscular tissue, thereby making its spinous process 15 accessible, whereas access to the lamina 16 requires detachment of muscular tissue.

In the state shown in FIG. 1A, using an instrument (not shown), it is possible to make in the area of the lamina 16 or in the area of the spinous process 15, in accordance with the invention, a single incision gap 20 or 22, which allows the vertebral arch 12 or its vertebral arch sections separated by the incision gap 20 or 22 to be elastically/plastically expanded, so that further areas of the vertebra need not be exposed.

The creation of the incision gap is not limited to any particular procedure. For example, the incision gap can be made with an ultrasonic osteotome, which enables particularly gentle splitting of the bone substance as far as the spinal canal 11. Here damage to the connective tissue of the spinal cord is avoided.

Alternatively, rapidly rotating drills may be used, but the last phase of the splitting incision up to the spinal cord is preferably carried out with a bone punch.

A further alternative is offered by the so-called T-saw or Gigli saw, with which the incision gap is made starting from the spinal canal 11.

Figure 1B:
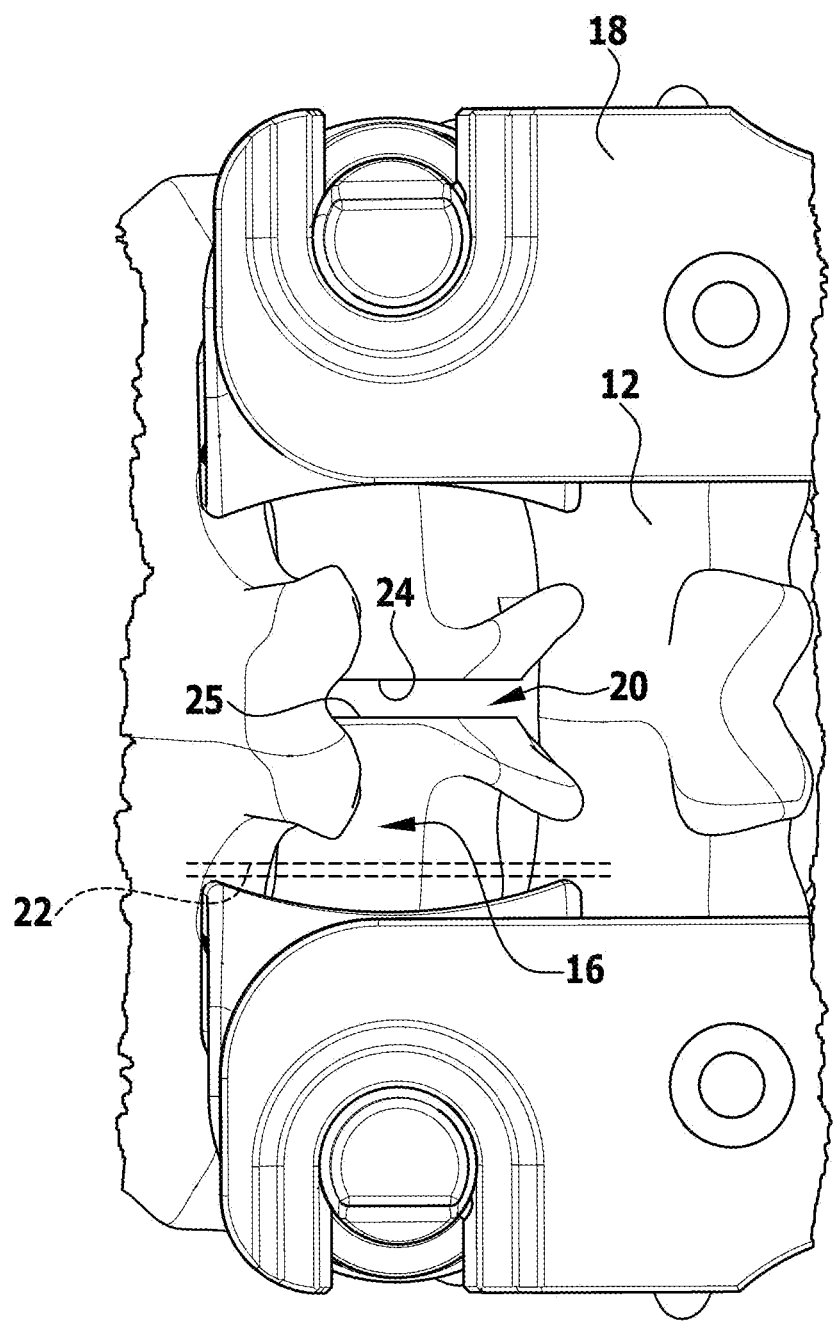

FIG. 1B shows the vertebra 14 with the incision gap 20 completed in the spinous process. The alternative incision gap 22 in the lamina of the vertebral arch 12 is shown in broken representation.

The invention will be described hereinbelow with reference to the incision gap 20 made in the spinous process, but as will be clear to the person skilled in the art an analogous procedure applies to the incision gap 22 in the lamina.

The incision gap 20 has two incision surfaces 24 and 25 arranged in parallel in the state shown in FIG. 1B. The gap width in this state depends on the technique used to make the incision gap and, for example, when an ultrasonic osteotome is used, is about 1 mm or less. An incision gap width of about 2 mm to 3 mm is typically obtained with rapidly rotating drills.

Figure 2:
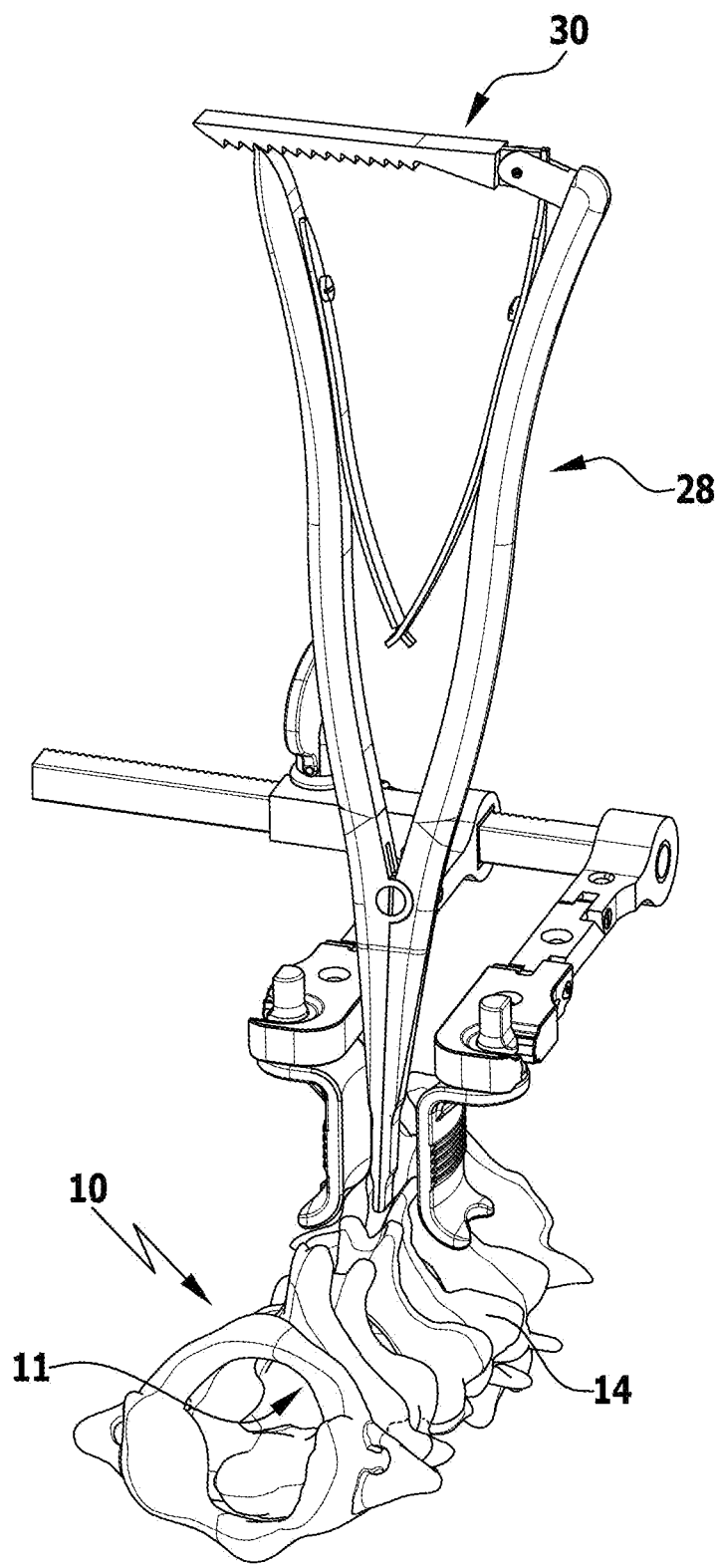
FIG. 2 shows the cervical vertebra of FIG. 1B during elastic expansion of the incision gap.

A distraction instrument 28 is used to elastically/plastically expand the incision gap 20 and is inserted dorsally into the incision gap 20, as shown in FIG. 2. The distraction instrument preferably has a gap width display and/or a force-measuring device (both not shown), so that the gap width obtained can be read off and/or the force used for the expansion can be applied in a metered manner. It is also preferable for the distraction instrument 28 to have a locking element 30 which automatically fixes an expanded position, once reached, of the distraction instrument. This locking element 30 may also facilitate a stepped expansion of the incision gap.

Figure 3:
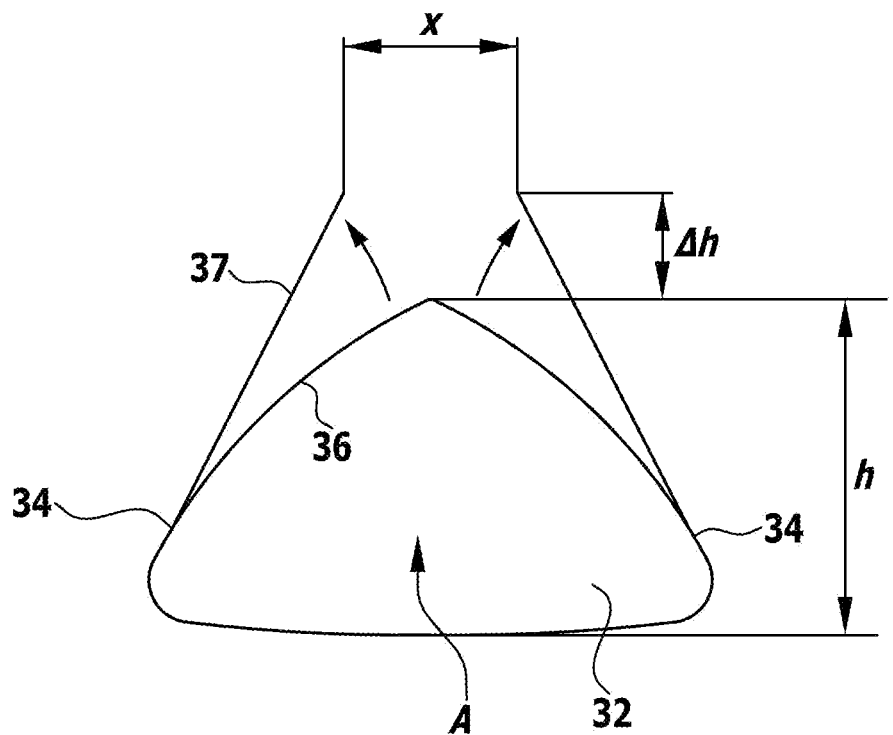
FIG. 3 shows a schematic sectional view through a vertebral canal elastically expanded in accordance with the invention.

The results in terms of expansion of the vertebral canal diameter or the vertebral canal area can be explained using a simple model shown in FIG. 3.

The starting point is a C6 vertebra with the parameters indicated in FIG. 3 A=150.65 mm$^2$ and a diameter h of 11.5 mm. The calculations for a corresponding gap width x are based on the following assumptions:

The shape of the spinal canal in the vertebra can be approximated by a bent triangle 32 as shown in FIG. 3.

The pivot point 34 of the vertebral arch sections lies in the area of the so-called facet joints or small feet.

The sole elastic/plastic deformation of the sections of the vertebral arch 12 is assumed in the area of the lamina, and, for reasons of simplicity, its arch length was assumed as constant and the bending lines 36, 37 were simplified as curves.

The vertebral body (not shown) and the points at which the lamina is connected to the vertebral body (small feet) are assumed to be rigid.

In the calculation, the width of the opening (gap width) x was increased in the range of 6 to 16 mm in 2 mm increments. The corresponding values for the increase in area ΔA and the increase in diameter Δh are listed in the following Table 1.

These values show that the value recommended in the literature (Wang, Xiang-Yang et al. in SPINE, Vol. 31, No. 34, 2006, pages 2863 to 2870) for the increase in diameter is achievable with the elastic/plastic deformation of the bone substance in accordance with the invention.

TABLE 1

| Width of gap x | Increase in area ΔA | Increase in diameter Δh |
| --- | --- | --- |
| 6 mm | 50.67 mm$^2$ | 3.79 mm |
| 8 mm | 63.30 mm$^2$ | 4.22 mm |
| 10 mm | 75.36 mm$^2$ | 4.53 mm |
| 12 mm | 86.72 mm$^2$ | 4.72 mm |
| 14 mm | 107.66 mm$^2$ | 4.99 mm |
| 16 mm | 126.84 mm$^2$ | 5.16 mm |

Figure 4A:
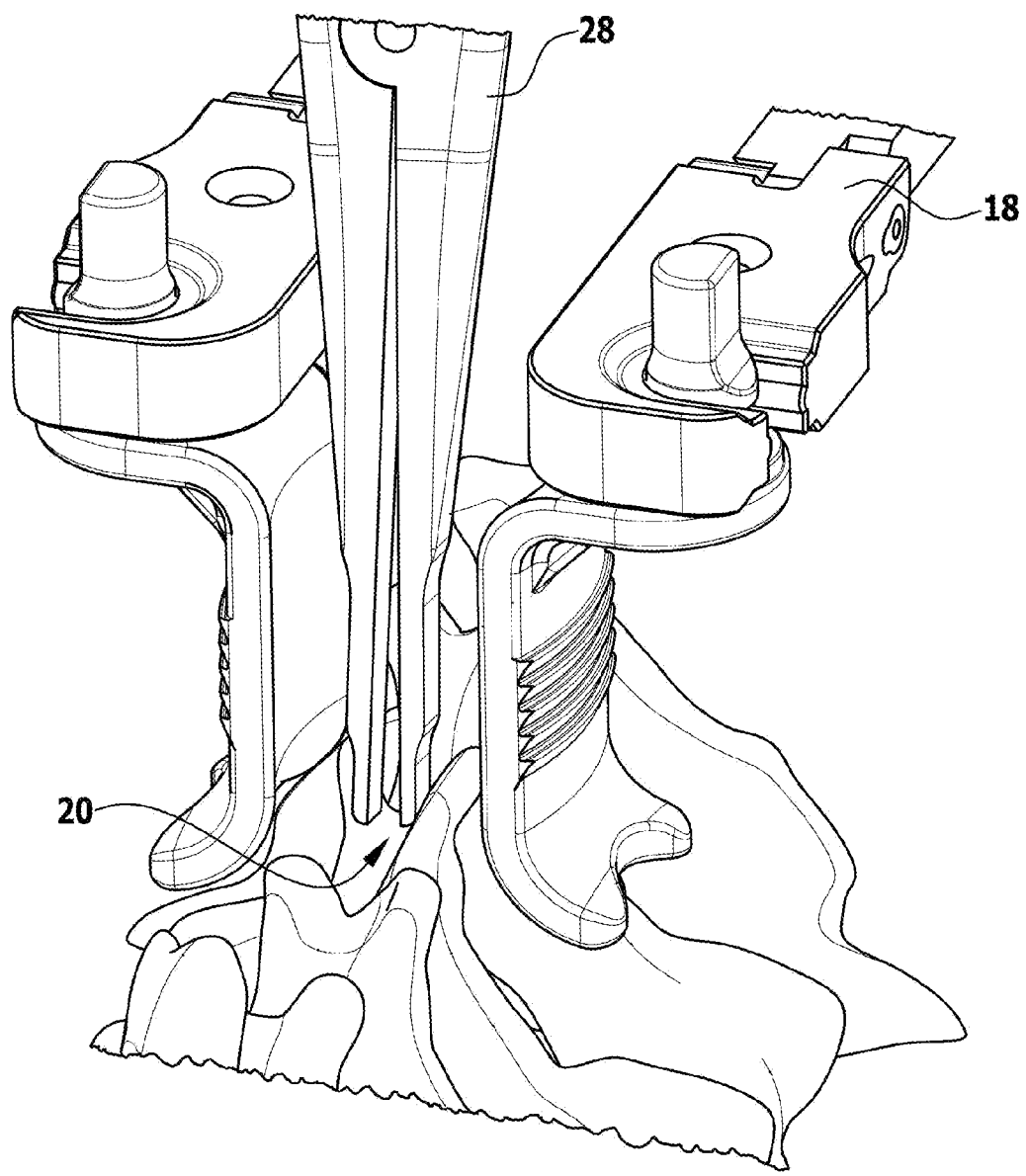
FIGS. 4A and 4B show detailed views of the cervical vertebra of FIG. 1B with alternative retractors.
Figure 4B:
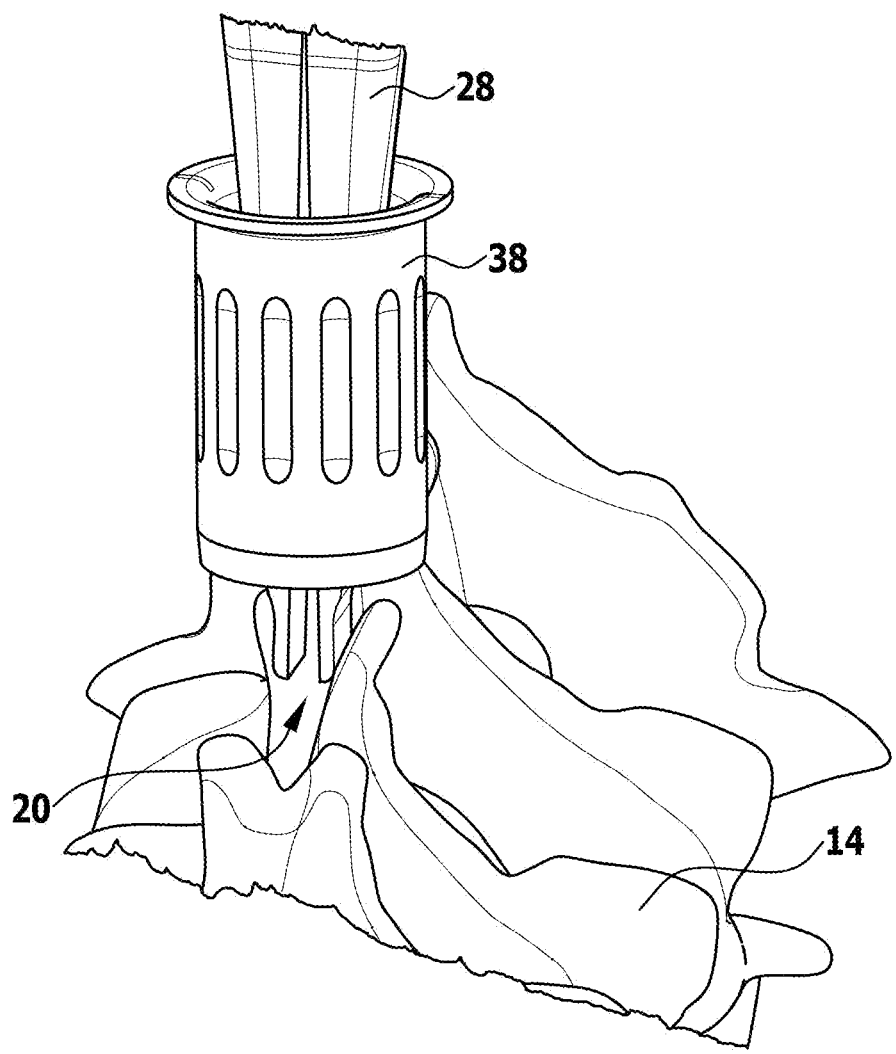

The partially already expanded incision gap 20 is shown in FIG. 4A together with the retractor 18 and in FIG. 4B with an alternative retractor which, in the simplest case, may have the shape of a sleeve 38.

In many cases, such a sleeve 38 is fully adequate to keep the operating site free, and it has the advantage that the latter is largely freely accessible in the surrounding area, whereas the retractor 18 requires more space, but has further advantages, as will be explained hereinbelow.

Figure 5A:
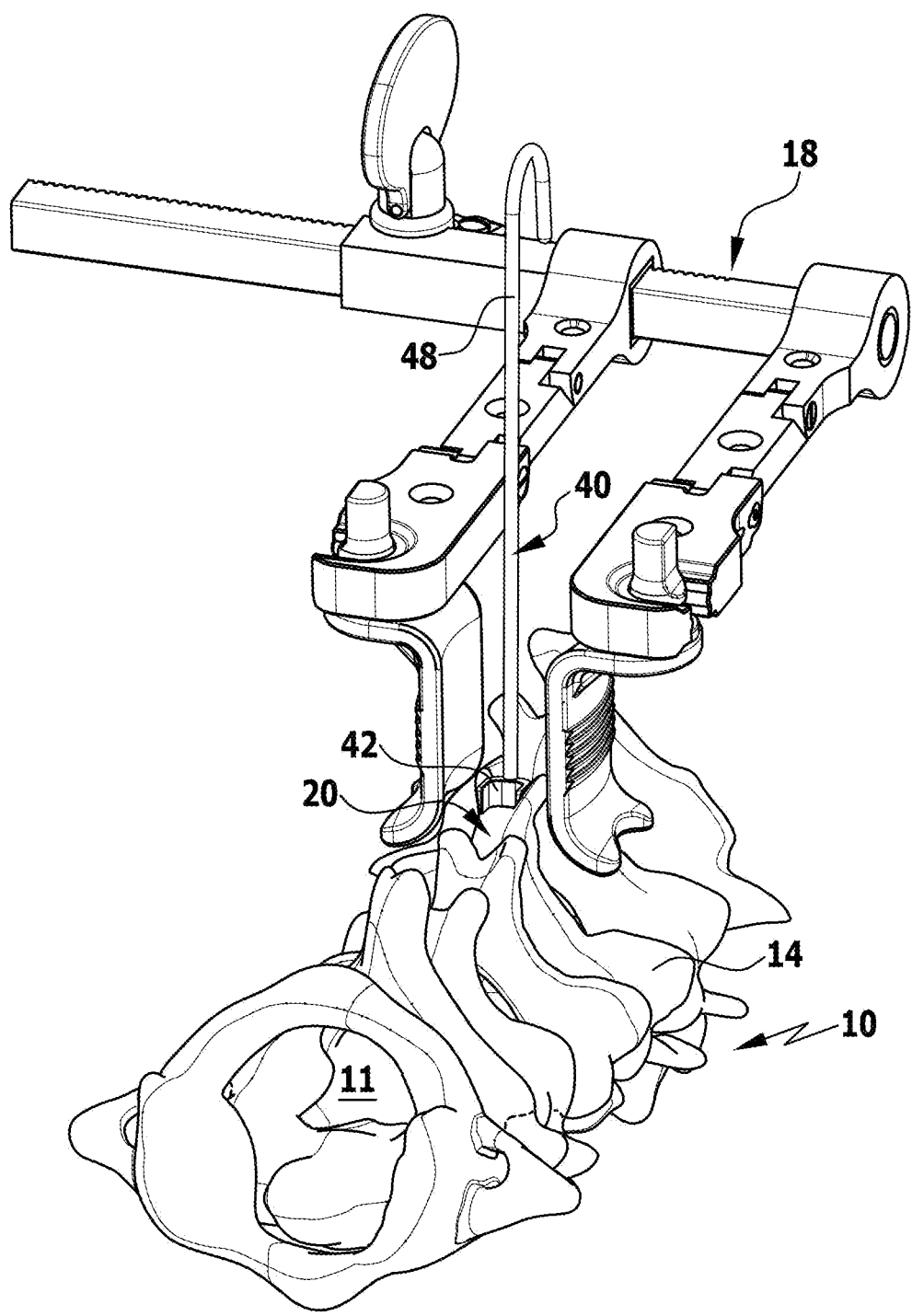
FIGS. 5A and 5B show vertebra with an incision gap expanded in accordance with the invention and with an inserted spacer.
Figure 5B:
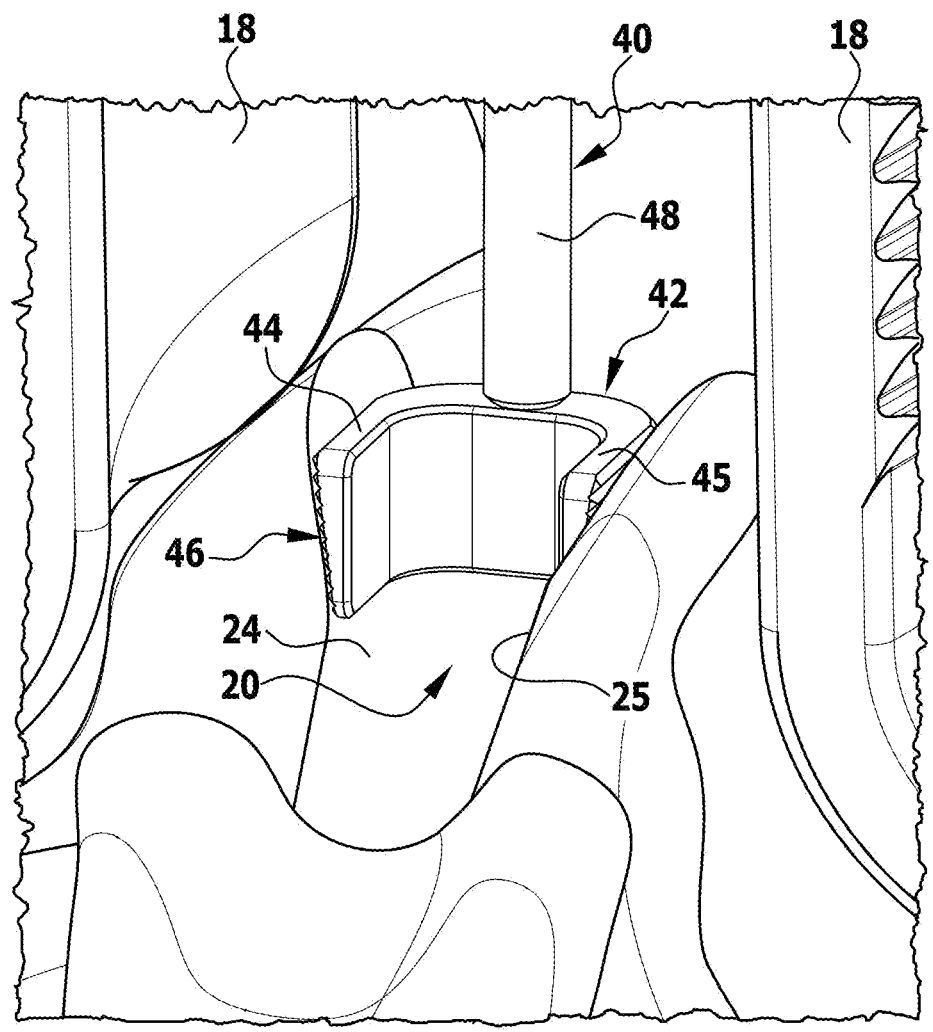

Once the incision gap 20 is sufficiently expanded, it can be stabilized in this form in accordance with a variant of the method in accordance with the invention by a spacer 40, as shown in FIGS. 5A and 5B.

The spacer 40 preferably comprises a spacer element 42 bent in the shape of a U, which holds the incision surfaces 24, 25 of the incision gap 20 at a prescribed spacing. In this state, the spinal canal is freely accessible in the area of the vertebra 14. The two legs 44, 45 of the U-shaped spacer element 42 are preferably configured so as to extend over a large area, so that the contact between the incision surfaces 24, 25 of the incision gap 20 and the spacer element takes place over as large an area as possible, and as small a surface pressure as possible results with the forces required for the elastic/plastic expansion of the vertebral canal. The preferred measure of arranging the outside surfaces of the spacer element 42 in the shape of a wedge at an incline to each other in accordance with the inclination of the incision surfaces 24, 25 of the expanded incision gap 20 also serves this purpose.

In order to hold the spacer element 42 as securely as possible in its position between the incision surfaces in the incision gap, the surfaces facing the incision surfaces 24, 25 have a plurality of parallel ribs 46, which counteract unintentional sliding of the spacer element out of the incision gap in the dorsal direction. Owing to the parallelism of the ribs 46, once the implant has been inserted into the incision gap 20, the spacer element 42 can be removed from the incision gap 20 in the sagittal direction without applying any great force.

The spacer element can be additionally secured in its position in which it is inserted in the incision gap by a stem-like holder 48 which is preferably formed on the arched part of the spacer element 42. When a retractor 18, as shown, for example, in FIG. 5A, is used, the holder 48 may, if required, be fixed to it.

Figure 6:
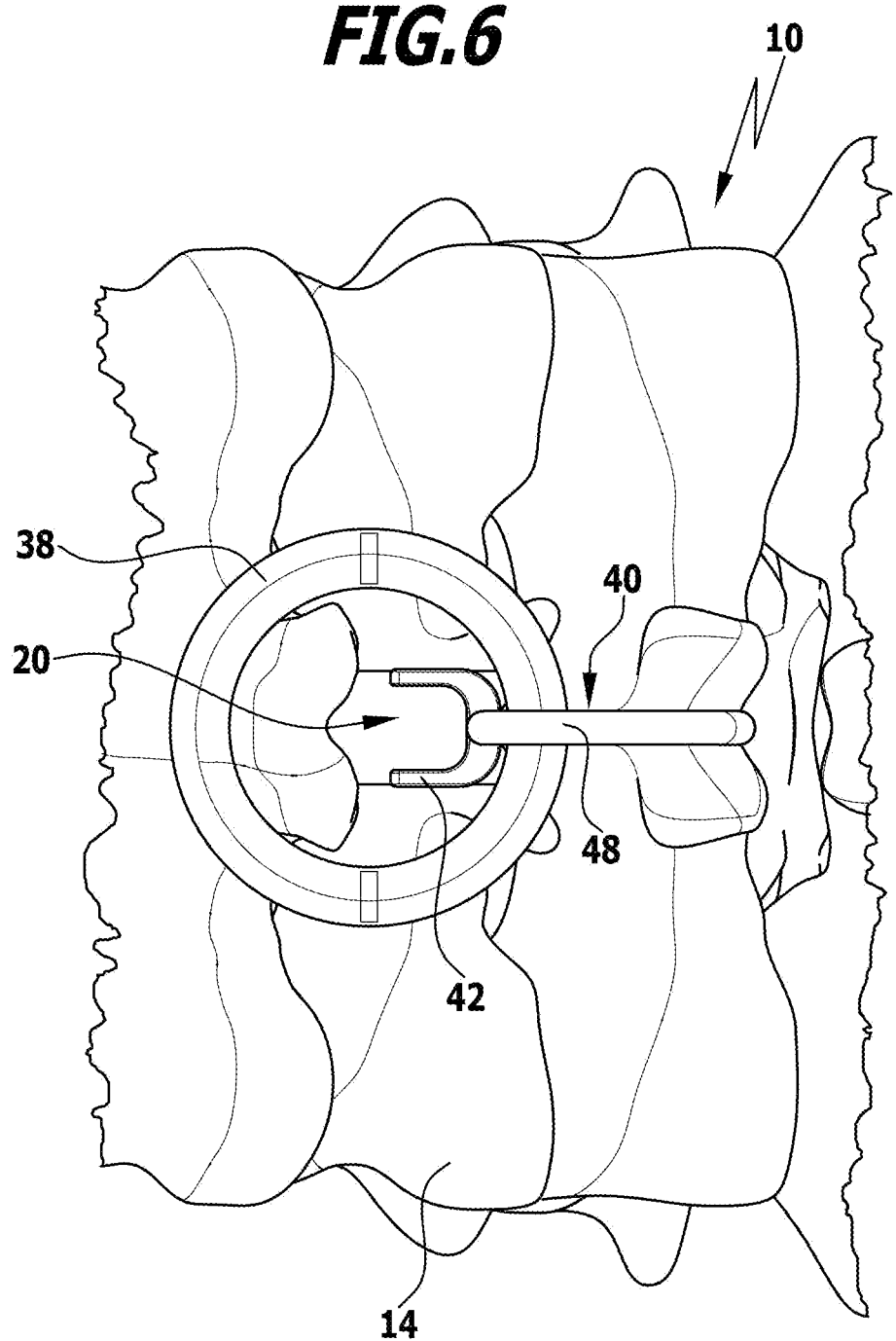
FIG. 6 shows a plan view of the vertebra in accordance with FIGS. 5A and 5B with an alternative retractor in a plan view of the expanded incision gap.

FIG. 6 shows the spacer 40 with the spacer element 42 positioned in the incision gap 20 when another type of retractor 38, as already described in conjunction with FIG. 4B, is used. FIG. 6 shows in a plan view the access to the spinal canal 11 created by the elastically expanded incision gap 20, which, of course, also results in the same way when a different type of retractor such as, for example, retractor 18, is used.

Figure 7A:
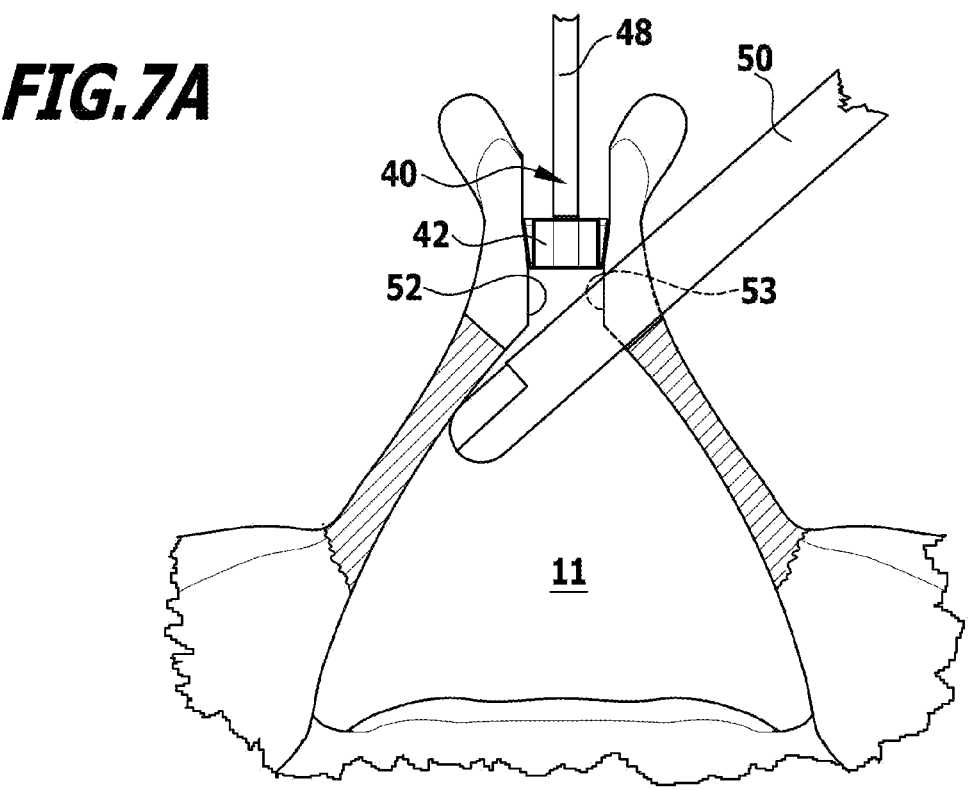
FIGS. 7A and 7B show an operative treatment in the vertebral canal with a spacer inserted in the incision gap.
Figure 7B:
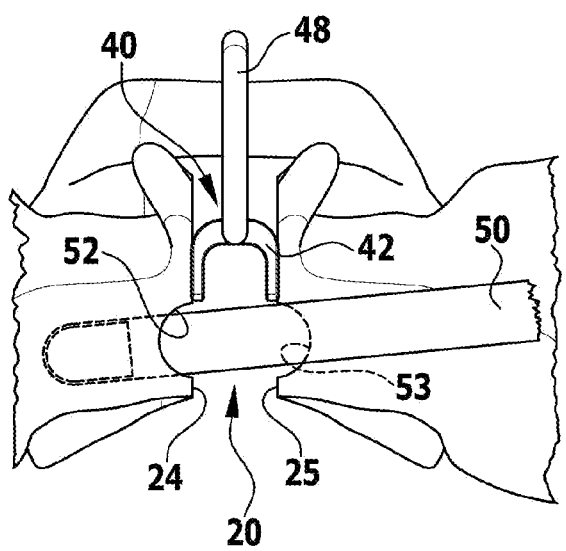

FIGS. 7A and 7B show schematically in a side view and a plan view, respectively, the possibility of access to the spinal canal 11 with a so-called shaver 50 by way of example. Given the same gap width, in order to create a greater operating range for use of surgical instruments, for example, a shaver or a punch, and to achieve further advantages which will be discussed hereinbelow, grooves 52, 53 are preferably formed in the incision surfaces 24, 25 of the incision gap 20, and it is further preferred for these to extend over the entire height of the incision surfaces 24, 25.

With the shaver 50, as shown in FIGS. 7A and 7B, it is, for example, possible to machine the lamina on the spinal canal side of the vertebral arch in order to create space for further decompression of the spinal cord.

This enables removal of bone substance on the spinal canal side of the lamina, in order to increase its elasticity and allow further expansion. In difficult cases, creation of a groove on sides of the spinal canal may also be considered, so that, similarly to the conventional double-door technique, the vertebral arch sections can be bent about a kind of hinge. In contrast to the conventional technique, this does, however, not require any removal of muscle from the spine, so that it is still a gentler surgical intervention.

Figure 8A:
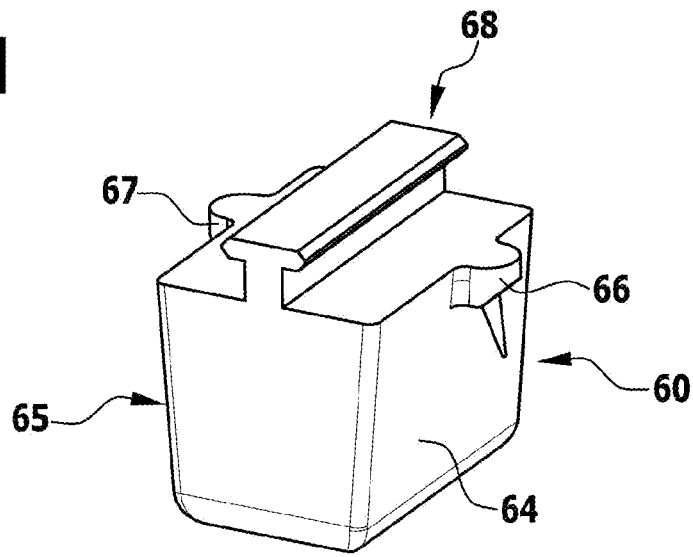
FIGS. 8A and 8B show basic shapes of a first embodiment of an implant in accordance with the invention.
Figure 8B:
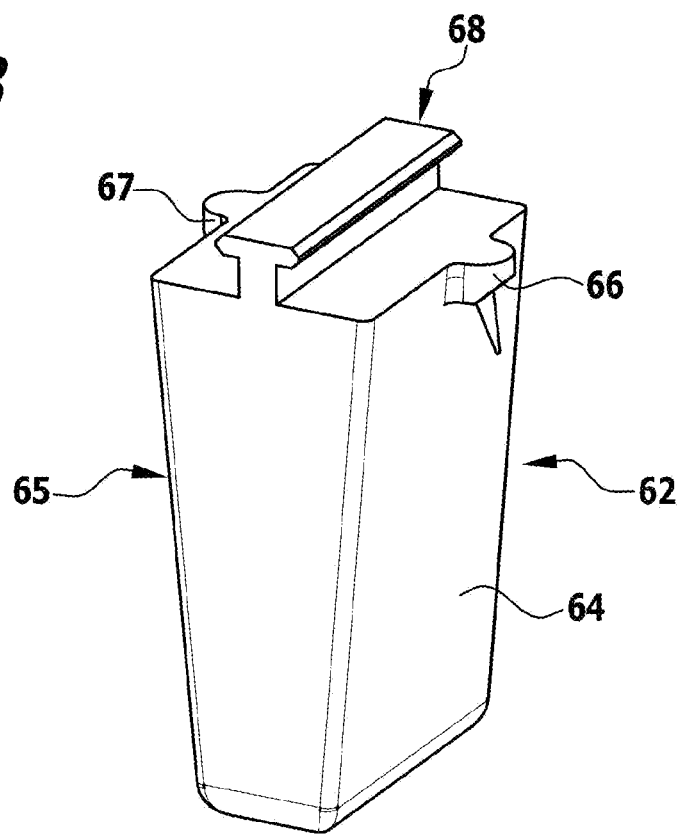

Once the expanded incision gap 20 is ready for insertion of an implant, an implant body 60 or 62, as shown, by way of example, in FIGS. 8A and 8B, is preferably inserted into the incision gap 20.

The two implant bodies 60, 62 are both of solid construction and are preferably produced from a plastic material suitable for implants, in particular, PEEK. The two implant bodies 60, 62 have contacting surfaces 64, 65 inclined in relation to each other, which, in the inserted state of the implant, are in contact over as large an area as possible with the incision surfaces of the incision gap. While the implant bodies 60, 62 are of wedge-shaped configuration in a front view, it is quite possible for them to be of substantially rectangular configuration in a side view.

The plastic material suitable for an implant (e.g. PEEK) is preferably coated, for example, by the Plasmapore technique or with a hydroxyapatite coating, to promote growth of the bone substance to the implant.

At their upper end in FIGS. 8A and 8B, which, in the inserted state of the implant, lies dorsally, the implant bodies 60, 62 have laterally protruding projections 66, 67 which may assume several functions:

Firstly, the projections 66, 67 have the effect that the implant can only be inserted into the incision gap up to the point at which the projections 66, 67 strike the bone substance, and a displacement of the implant in the direction of the spinal canal is also prevented in the postoperative phase.

Furthermore, the projections 66, 67 in positively locking engagement with an instrument or with corresponding recesses in the bone substance may act so as to guide the implant body during insertion of the implant into the incision gap and thereby assist precise placement.

Finally, the projections enlarge the dorsal area of the implant body and therefore facilitate accommodation of holding elements such as, for example, screws, spikes, etc., which serve to fix the implant in the expanded incision gap.

A bar 68 undercut on both sides is formed as grip element on the implant bodies 60, 62 so as protrude dorsally therefrom. The bar 68 serves for easier handling during insertion and correct positioning of the implant.

The contacting surfaces, arranged in wedge-shaped configuration at an incline to each other, of the implants used in accordance with the invention preferably define an angle of about 5° to about 45°, in particular, about 7° to about 30°, between them.

In the example shown here, the angle is about 10°.

FIG. 9 shows the procedure of inserting the implant body 62 into the incision gap 20, which is held by a spacer 40 in the expanded state. In order to create sufficient space for insertion of the implant, the spacer 40 may be moved to some extent out of the incision gap in the sagittal direction so that only quite small surface areas of the legs of the spacer element 42 remain in contact with the incision surfaces 24, 25 of the incision gap 20. The implant is then inserted, as shown in FIG. 9, with forceps 70 at a slight incline to the incision gap axis S into the incision gap 20.

After complete removal of the spacer 40, the implant body 62 is brought into its final position, as shown in FIG. 10. In this example, the height of the implant body 62 is selected such that, in the inserted state, it does not quite reach the spinal canal with its ventrally located end, so that an additional volume remains there for decompression of the spinal cord.

Figure 11:
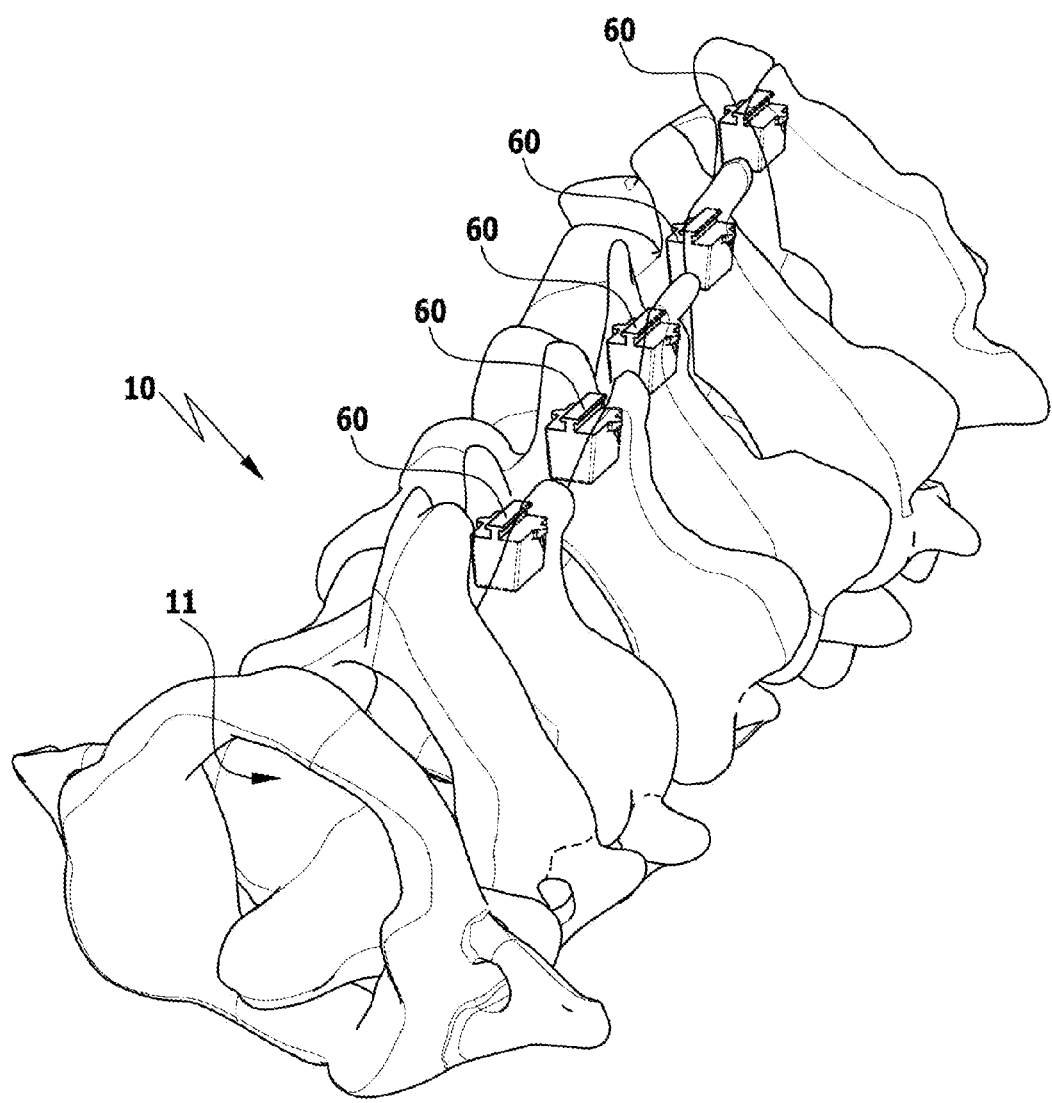
FIG. 11 shows a section of the cervical vertebra in a schematic representation with implants inserted in accordance with the invention.

Finally, FIG. 11 shows in a schematic representation a section of the cervical spine with vertebrae C1 to C7 with expanded vertebral canals which are permanently secured in the expanded state by an implant 60 in each case.

FIG. 12 shows a further embodiment of an implant body 80 in accordance with the invention in a perspective view, a plan view and a front view. The implant body 80 again has the shape of a wedge with contacting surfaces 82, 83 at an incline to each other, which, in the inserted state, bear over a large area against the incision surfaces of an incision gap.

These implant bodies 80 preferably have at their contacting surfaces semi-cylindrical projections 84, 85 which extend over almost the entire height of the implant body 80. Formed in the correspondingly prepared incision gap are, therefore, complementary grooves (not shown here) which guide the implant when it is being inserted. If the grooves are only used for guiding the implants, these are then preferably not formed continuously right up to the vertebral canal, so that a stop against which the projections 84, 85 bear is produced in the bone material of the incision surfaces for insertion of the implant 80. The implant bodies 80 are thereby prevented from being inserted too deeply into the incision gap or the implant body 80 is prevented from becoming displaced in the direction of the spinal canal at a later point in time and from causing compression there.

From the plan view of FIG. 12 it can be clearly seen that the projections 84, 85 are arranged eccentrically in the sagittal direction of the implant. This offers the advantage that the corresponding recesses in the vertebral arch can be formed at least to a considerable extent outside the area of the spinous process.

If the implant is fastened in the bone substance with fastening elements such as, for example, screws, dowels, bolts or splints, as will be described in conjunction with the embodiments of FIGS. 23 and 24, access for their insertion is then easier.

The terms dorsal and ventral used in conjunction with the description of the implant bodies correspond to the terms proximal and distal, respectively, as seen by the surgeon.

FIG. 13 shows a first embodiment of a multiple implant 90 which is suited for insertion as one implant into incision gaps made in successive vertebrae. The shape of the multiple implant 90 corresponds substantially to the implant 80 in relation to the implant areas 92, 93, 94 or incision gaps provided per vertebra. The implanted state is shown schematically by way of example in a section of the cervical spine 10 in the plan view. As the implant areas are essentially fixedly connected to one another, they thus result in a stabilization and a certain immobilization of the treated section of the spine.

Figure 14:
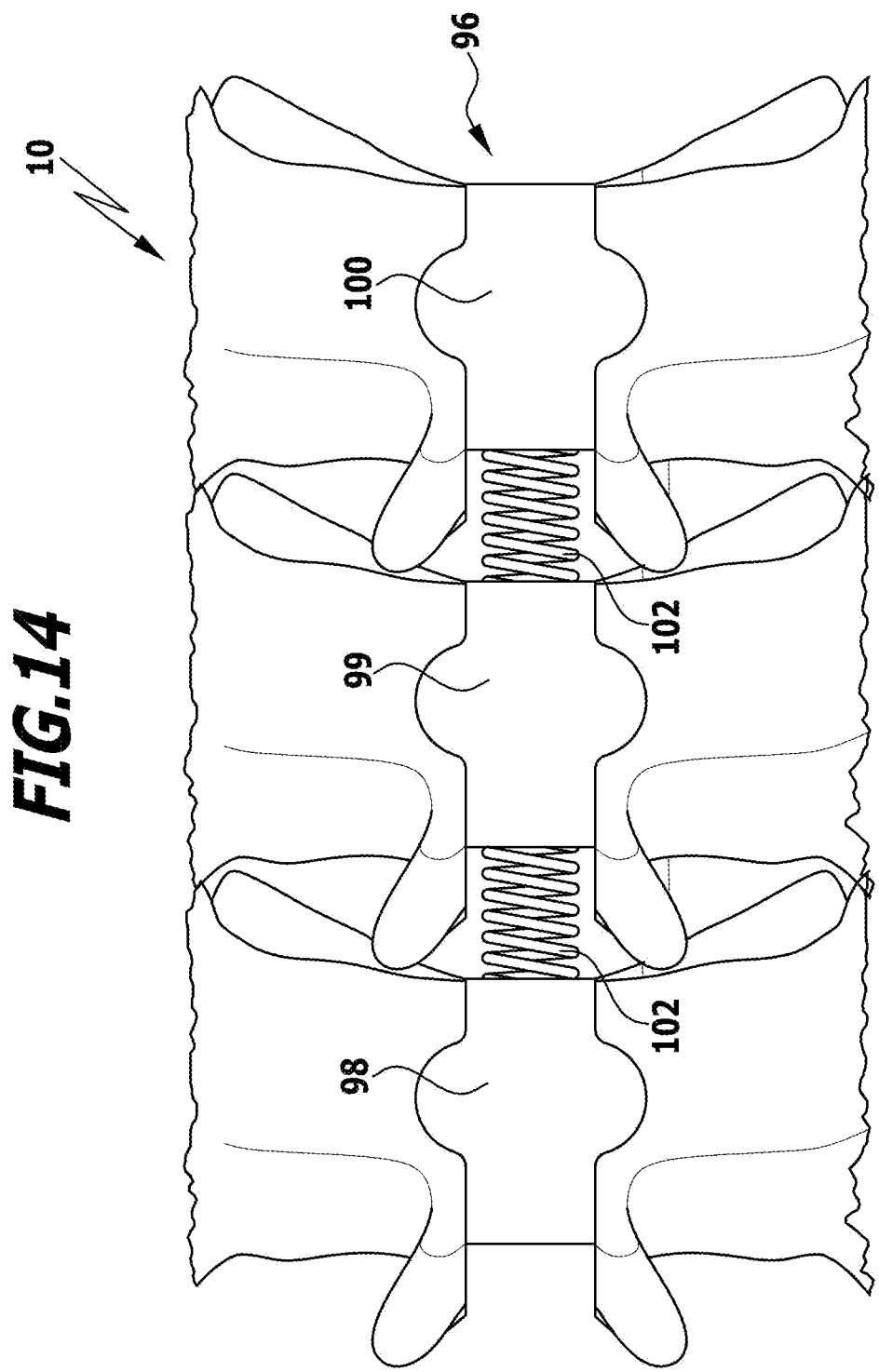
FIG. 14 shows a second embodiment of a multiple implant in accordance with the invention in the implanted state.

FIG. 14 shows a second embodiment of a multiple implant 96 in which the individual implant sections 98, 99, 100 are not fixedly, but movably connected to one another. Such a connection may, in particular, be of articulated configuration and, further preferred, as shown in FIG. 14, of elastic configuration in the sagittal direction, for example, by means of helical springs 102. Here, too, stabilization of the treated section 10 of the spine occurs, but without the immobilization which in many cases is undesired.

Figure 15:
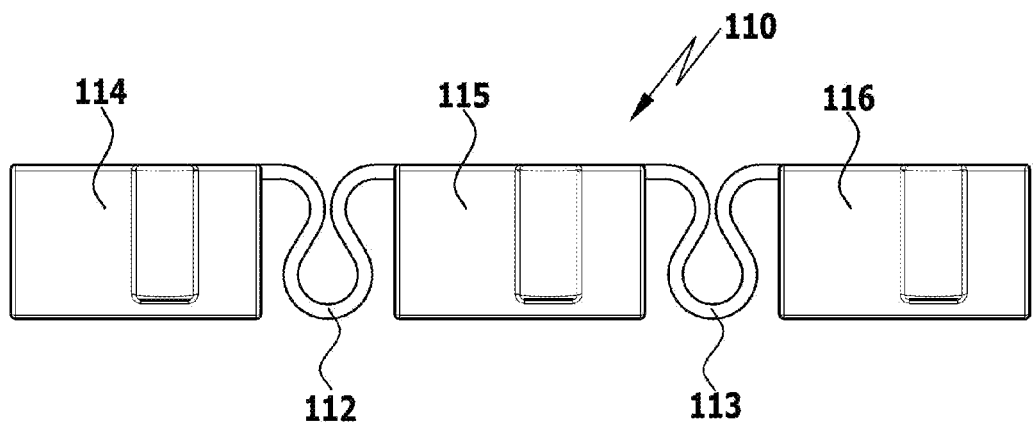
FIG. 15 shows a third embodiment of a multiple implant in accordance with the invention in a side view.

A variant of the multiple implant 96 of FIG. 14 is shown in FIG. 15. The multiple implant 110 shown therein has instead of the helical springs 102 leaf springs 112, 113 for coupling the implant sections 114, 115, 116 to one another movably and resiliently.

Figure 16:
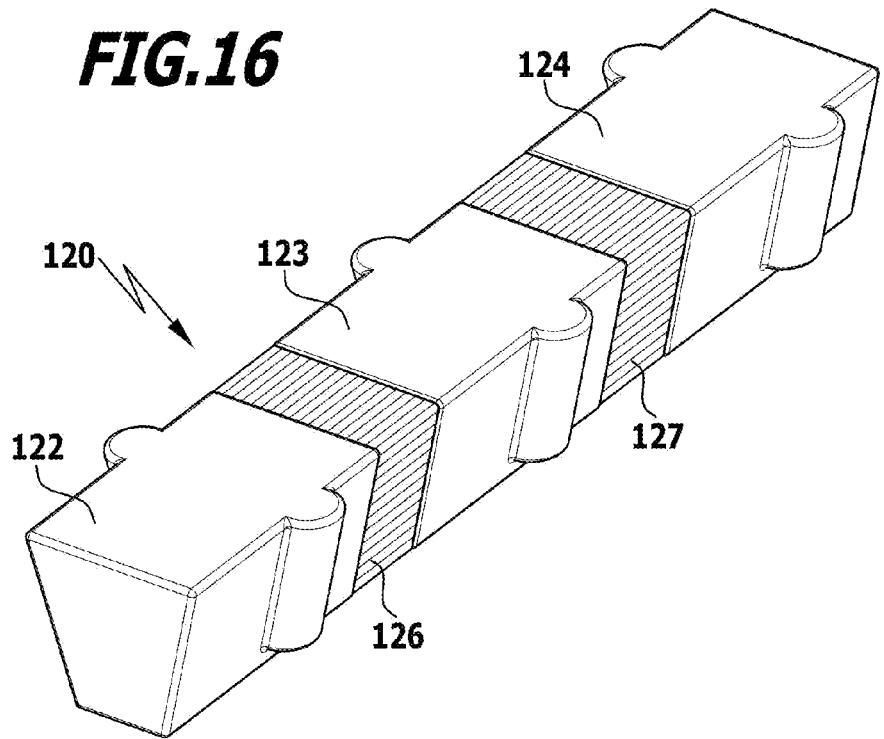
FIG. 16 shows a fourth embodiment of a multiple implant in accordance with the invention in a perspective representation.

A further variant of the multiple implant 96 of FIG. 14 is shown in FIG. 16. In this multiple implant 120, the elastic connection between the individual implant sections 122, 123, 124 is made by elastomer bridges 126, 127. The elastomer bridges 126, 127 can be so adjusted in their elasticity that the desired freedom of movement is maintained between the individual vertebrae, but excessive movements which might adversely affect the success of the treatment are hindered or even prevented.

Figure 17A:
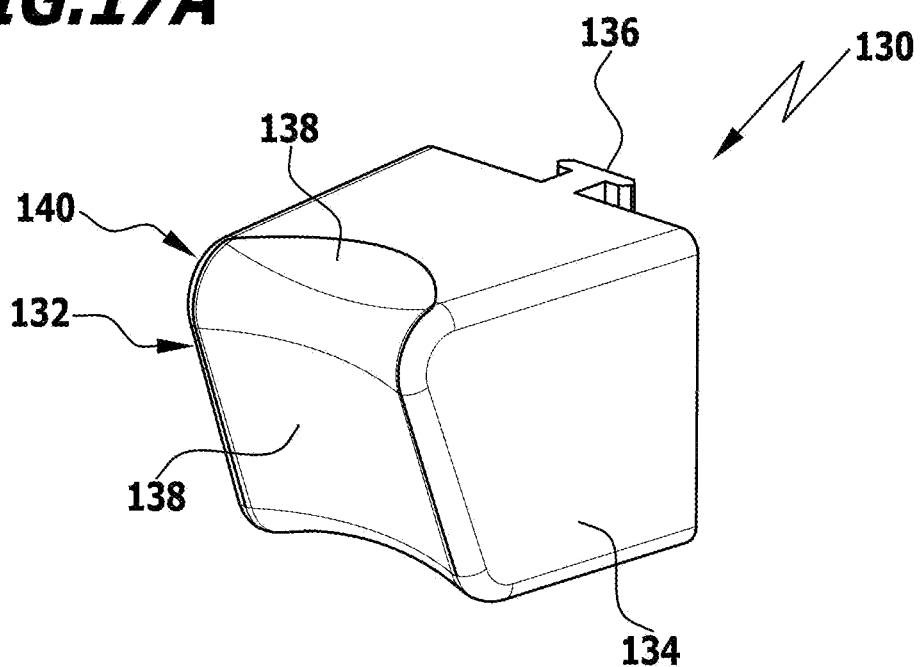
FIGS. 17A and 17B show a third embodiment of the implant in accordance with the invention in a perspective view and a side view.
Figure 17B:
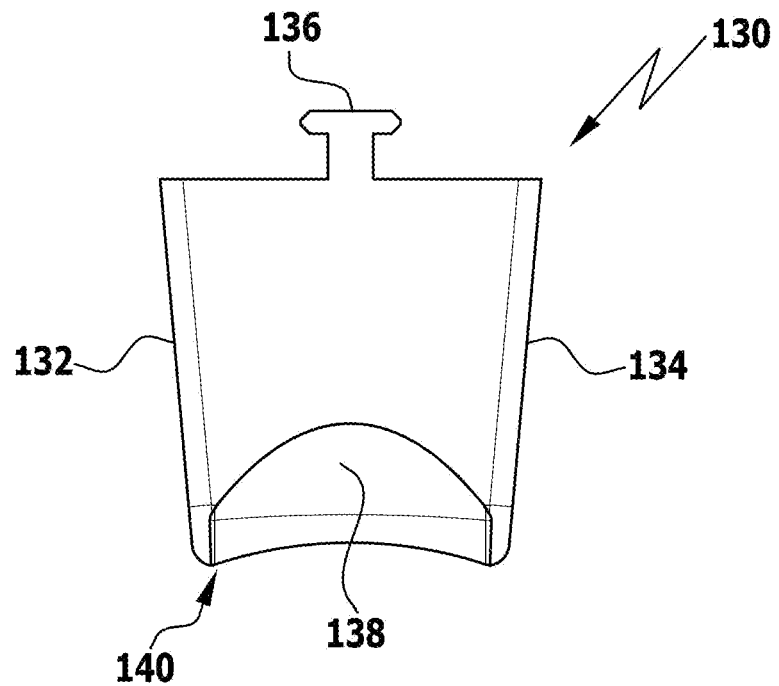

FIGS. 17A and 17B show individually the detailed configuration of a preferred implant body 130 in accordance with the invention, which, like the previously discussed preferred implant bodies, has bearing surfaces 132, 134 aligned in the shape of a wedge in relation to each other, which, in the inserted state in the incision gap, come to bear against its incision surfaces. There is formed at its dorsal end a grip bar 136 with which the implant can be inserted precisely into the incision gap.

On its ventral side, the implant body 130 has an indentation 138 which extends around the ventrally protruding edge 140 and allows a further enlargement of the space available on the spinal canal side and therefore further decompression of the spinal cord. With this measure, the implant body 130 enables an additional gain in space for the spinal canal, which otherwise could only be achieved by a substantially greater spreading of the vertebral arch.

Figure 18A:
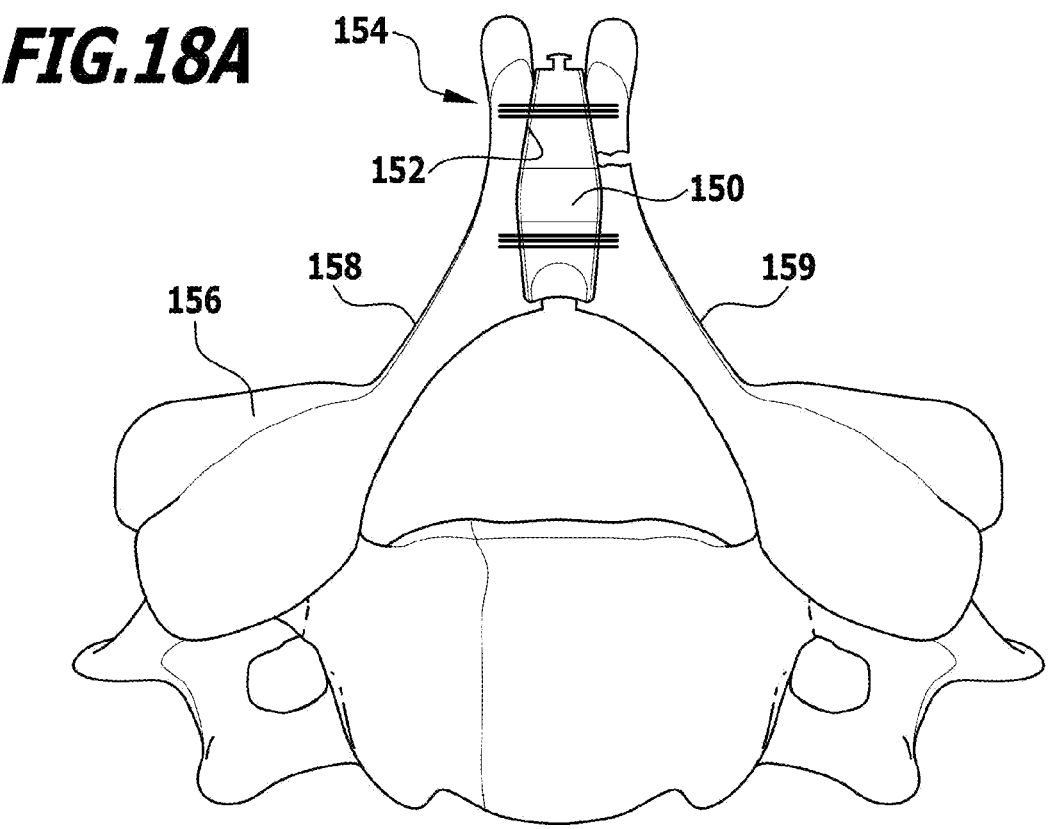
FIGS. 18A and 18B show a fourth embodiment of the implant in accordance with the invention in the implanted state in a side view.
Figure 18B:
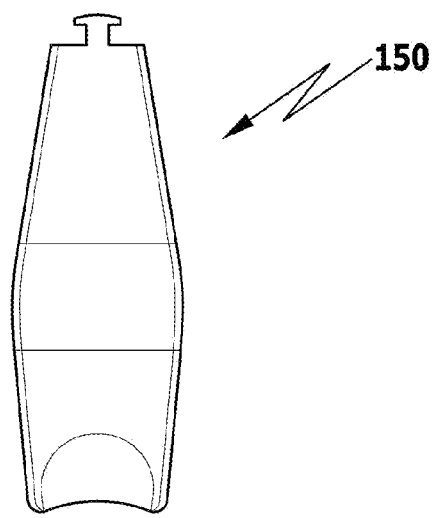

FIGS. 18A and 18B show a variant of the implant body 130. In this variant, the implant body 150 has a greater height, which may, for example, be twice the height of the implant body 130, so that it assumes the shape of a double wedge. In the inserted state in a incision gap 152 of a split spinous process 154 of a vertebra 156, the ventrally arranged part, which corresponds essentially to the shape of the implant body 130, as described in conjunction with FIGS. 17A and 17B, is positioned in the area of the incision gap on which the vertebral arch sections 158, 159 border. The dorsally arranged part is arranged between the parts of the split spinous process 154.

This variant of the implant body 150 has the advantage that, for example, a fractured piece of the spinous process 154 can be attached again so that it is possible for the fractured piece to grow together again. From a cosmetic point of view, a better outcome of the operation is also achieved here.

Figure 19:
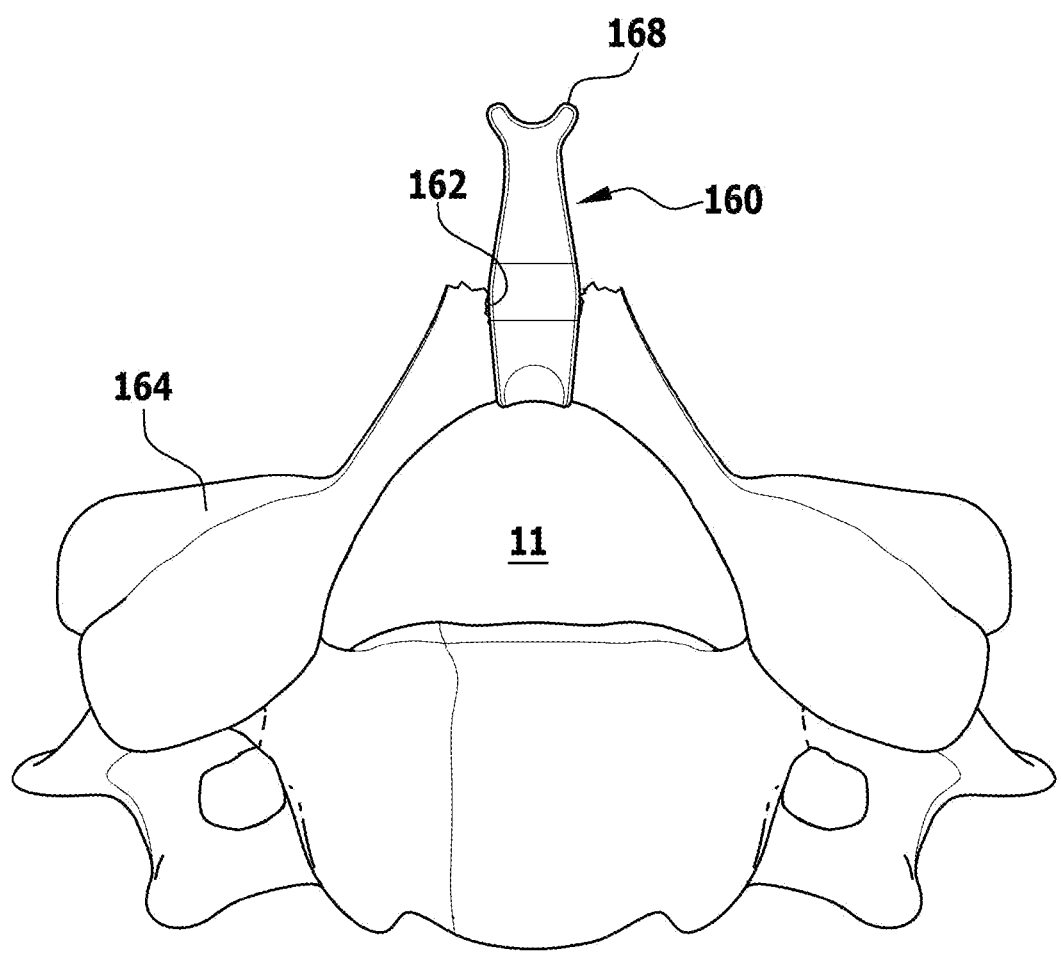
FIG. 19 shows a fifth embodiment of the implant in accordance with the invention in the implanted state in a side view.

The implant body 160 of FIG. 19 was developed from a similar point of view. It can be used in operations in which the spinous process must be partially removed. FIG. 19 shows the implant body 160 inserted in the incision gap 162 of a vertebra 164. The posterior end 168 (dorsal) of the implant body 160 reproduces the pre-operative shape of the spinous process and in spite of the removed parts of the spinous process thereby achieves a cosmetically satisfactory outcome after the operation. Furthermore, this shape of the implant offers the possibility of reattaching detached muscles.

Figure 20:
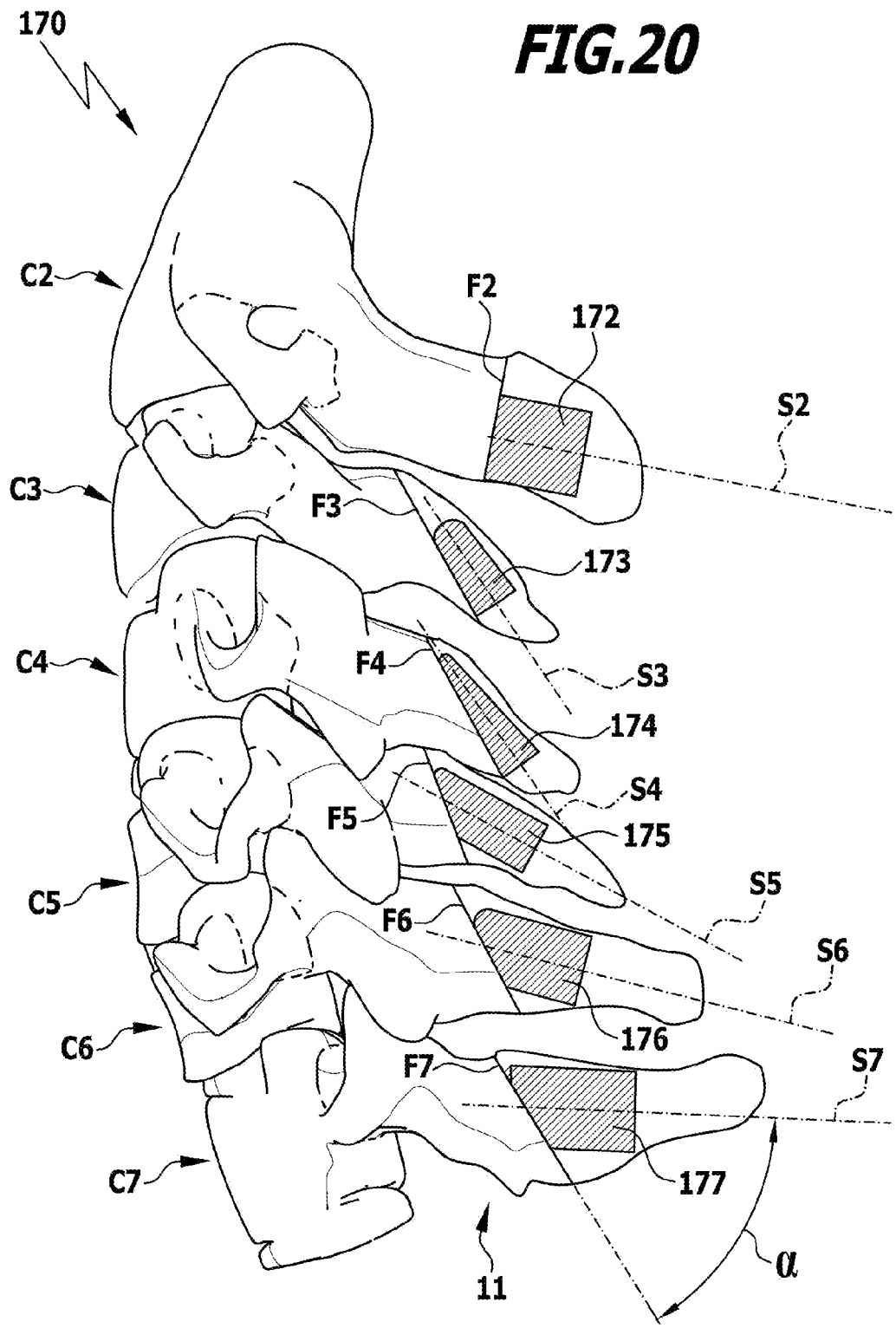
FIG. 20 shows implants in accordance with the invention of FIG. 17 in the implanted state in vertebrae of the cervical spine in a partly broken-open side view.

FIG. 20 shows a side view in partly broken-open (along the incision gap 20) form of a cervical spine section 170 in which the cervical vertebrae C2 to C7 are each held with an implant body 172, 173, 174, 175, 176, 177 in the expanded state of the vertebral canal. Depending on shape and size of the spinous process of the respective cervical vertebrae C2 to C7, implant bodies 172 to 177 of different size and different shape are used. These are inserted with their longitudinal axis, in each case, in substantially parallel alignment to the longitudinal axis S2, S3, S4, S5, S6, S7 of the spinous process.

The rear wall of the spinal canal 11 is designated by F2 to F7 in the cervical vertebrae C2 to C7. It represents, in each case, the dorsal boundary of the spinal canal and the anterior boundary of the lamina.

For optimum matching of the implant bodies to the respective vertebra, a large, diamond to rectangular cross section is, for example, required for the C2 vertebra, the C3 and C4 vertebrae require a long and rather flat, wedge-shaped cross section, whereas rather short and thicker wedge shapes of the implant bodies 176, 177 are required for the C6 and C7 vertebrae.

Figure 21:
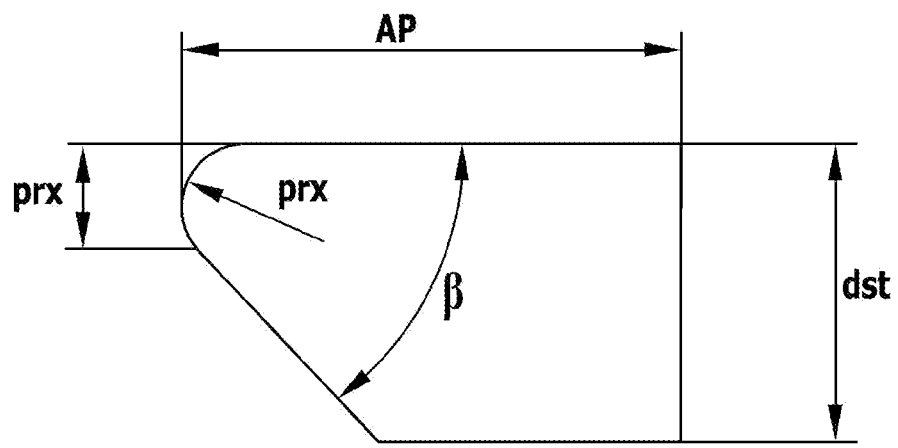
FIG. 21 shows a schematic representation of an implant body for definition of parameters.

The individual parameters which characterize these implant bodies are shown in FIG. 21 and indicated numerically by way of example in Table 2.

TABLE 2

| | Width dst | Length AP | Inclination β [°] | Remaining width prx | Radius prx | α [°] |
|---|---|---|---|---|---|---|
| C2 | 8.381 | 10.324 | — | — | — | 72.61 |
| C3 | 4.611 | 9.686 | 16.51 | 1.508 | 1.508 | 33.4 |
| C4 | 4.031 | 12.963 | 12.96 | 1.682 | 0.841 | 36.41 |
| C5 | 5.249 | 12.963 | 39.83 | 1.015 | 0.58 | 55.24 |
| C6 | 7.018 | 11.629 | 47.65 | 2.407 | 1.479 | 69.84 |
| C7 | 7.917 | 12.325 | 56.48 | 2.088 | — | 81.19 |

The angle α is defined as angle formed between the rear wall F2 to F7 (generally Fi) and the respectively associated longitudinal axis S2 to S7 (generally Si).

When expanding the incision gap 20, in accordance with the invention, a distraction tool is preferably inserted by the surgeon from a cranial position into the incision gap. Distraction tools which have at their distal end outwardly protruding flanges or ribs which are guided at the rear wall Fi are preferably used for this. In this case, the rear wall Fi serves as depth stop.

When inserting the implant with an insertion tool, the distraction tool positioned in the incision gap and/or the rear wall Fi of the spinal canal may serve the purpose of alignment along the longitudinal axis Si of the respective spinous process, for example, when the implant inserted in the incision gap is turned about the stop formed by the distraction tool.

Figure 22:
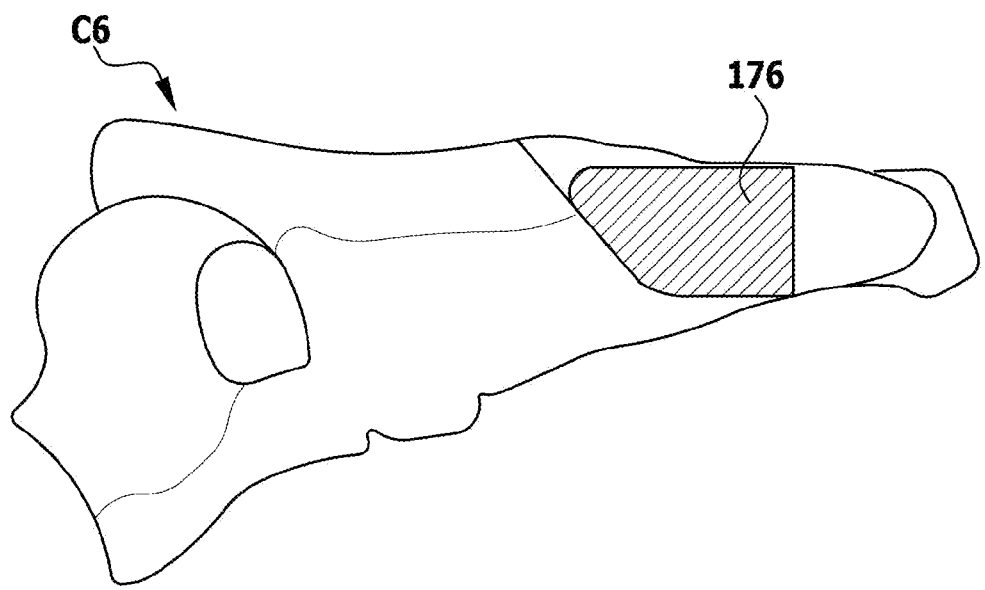
FIG. 22 shows a detailed view of an implanted implant in accordance with the invention of FIG. 17 in a partly broken-open representation of the vertebra.

Using the C6 implant 176 as example, FIG. 22 shows its installed situation in the incision gap of the spinous process of the C6 vertebra in a broken-open representation of the spinal canal.

Figure 23:
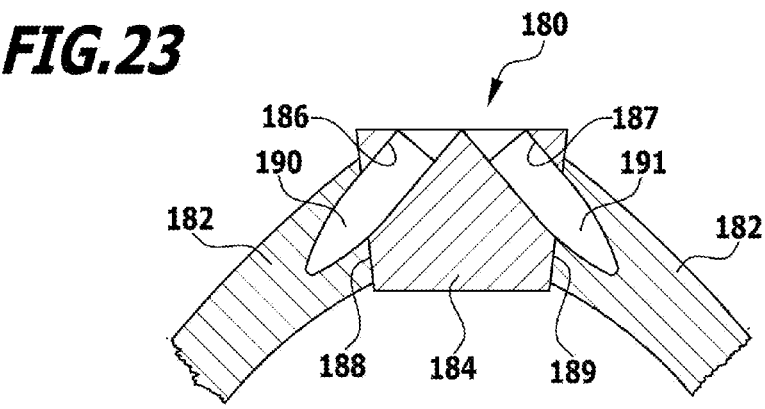
FIG. 23 shows a schematic sectional view of an implant fixed in accordance with the invention in the incision gap.

FIG. 23 shows a sectional representation of the installed situation of an implant 180 in accordance with the invention in the incision gap of a vertebral arch 182. There are provided in the implant body 184 two bore holes 186, 187 which extend at an acute angle to the contacting surfaces 188, 189 of the implant body 184, with which the implant body 184 bears against the incision surfaces of the incision gap of the vertebral arch 182. The bore holes 186, 187 extend from the dorsal surface of the implant body 184 and emerge from the contacting surfaces 188, 189.

In relation to the sagittal plane of symmetry, the bore holes 186, 187 are preferably arranged at an angle ranging from about 10° to about 60°, in particular, about 15° to about 45°. The angles are specified, above all, bearing in mind that as long a bore or thread section as possible is to be produced in the bone substance of the vertebral arch and that, at the same time, a fastening element inserted in the bore or thread section, such as, for example, a screw, a dowel, a bolt or a splint, is not to penetrate into the spinal canal. The longer the bore section or the thread section can be made in the bone substance, the more securely can the implant be anchored there.

Where the implant has a wedge shape, with the contacting surfaces that are inclined in the shape of a wedge in relation to each other forming an angle of, for example, 10°, angles of the axes of the bore or thread sections in relation to the plane of symmetry of the implant in the sagittal direction of about 20° to about 30° have, in many cases, proven advantageous.

If the implant 180 is fixed in the vertebral arch 182, pointed bolts 190, 191 are inserted in the bore holes 186, 187. In the installed state, the bolts 190, 191 exit with their point through the contacting surfaces 188, 189 and penetrate into the surrounding bone substance of the vertebral arch 182.

The bolts 190, 191 may differ in configuration. In accordance with one embodiment, the bolts 190, 191 may consist of a plastifiable material and are plastified for a short time in the inserted state so that a positively locking connection is produced between the material of the bolts 190, 191 and the bone substance of the vertebral arch 182 surrounding them at their points.

In accordance with another embodiment, the bolts are configured as so-called spikes and are retained in the implant body 184 and the adjoining portions of the bone substance of the vertebral arch 182 substantially with force locking.

In accordance with a further variant which will be described more specifically in conjunction with FIG. 24, the bolts 190, 191 are configured as threaded bolts, which are screwed with their point into the bone substance bearing against the contacting surfaces 188, 189.

Figure 24A:
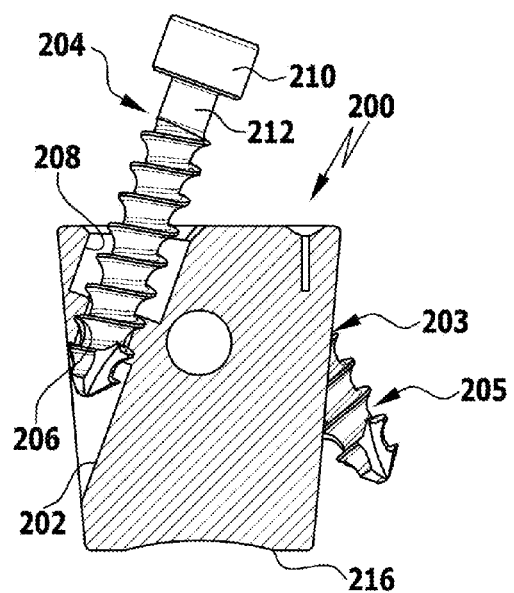
FIGS. 24A and 24B show a sixth embodiment of an implant in accordance with the invention.
Figure 24B:
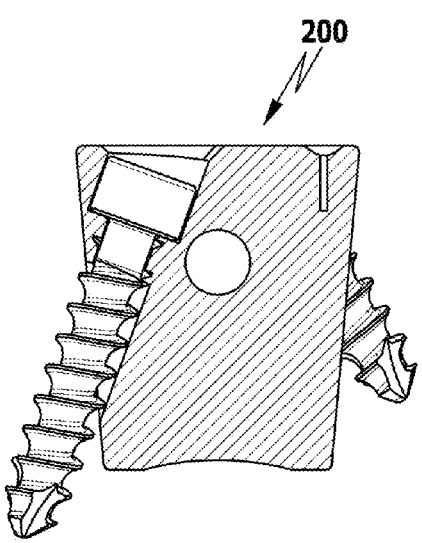

Illustration A of FIG. 24 shows a sectional view through an implant body 200 which—similarly to how this was described for FIG. 23—has two through-openings 202, 203 extending at an acute angle to the contacting surfaces of the implant body 200. The two through-openings 202, 203 are in staggered arrangement, so that only the through-opening 202 located at the front in the drawing is fully visible in the sectional representations of FIG. 24. Arranged in both through-openings 202, 203 are threaded bolts 204, 205, of which threaded bolt 205 is already fully screwed into the through-opening 203 and with its pointed end penetrates beyond the contacting surface into the bone substance of a vertebral arch (not shown here).

In illustration A of FIG. 24, the threaded bolt 204 is still shown in its initial position in which it is held with positive locking by a short thread section 206 forming part of the through-opening 202.

After insertion of the implant body 200 into an incision gap of a vertebral arch, the two threaded bolts 204, 205 are actuated and the implant 200 thereby screwed to the surrounding bone substance. The thread section 206 together with the remaining parts of the through-opening 202 guides the threaded bolts so that they can penetrate the surrounding bone substance with a predefined orientation.

The through-openings 202, 203 have at their dorsally located openings at the surface of the implant 200 a larger diameter, so that in the screwed-in state the threaded bolts 204, 205 can be fully accommodated with their bolt head 210 within the body of the implant 200. This area 208 of extended diameter of the through-opening 202, 203 is followed by the previously mentioned section with an internal thread 206.

The threaded bolts 204, 205 are preferably so configured that there is provided at their area adjacent to the bolt head 210 a so-called free-running section 212, which is long enough to pass through the internal thread 206 of the through-opening 202 so that when the threaded bolts 204, 205 are fully screwed in, the thread of the threaded bolts becomes disengaged from the internal thread 206, and, as a result, by tightening the threaded bolts 204, 205, the implant body 200 can be made to bear tightly with its contacting surfaces against the incision surfaces of the bone substance.

The length of the threaded bolts 204, 205 is of such dimensions that even after they have been screwed fully into the implant body 200, they do not protrude far enough from the implant body to be able to penetrate the spinal canal. In the fully screwed-in state, the point of the threaded bolts 204, 205 is, therefore, preferably positioned so as to remain behind the ventral front edge 216 of the implant 200.

Figure 25A:
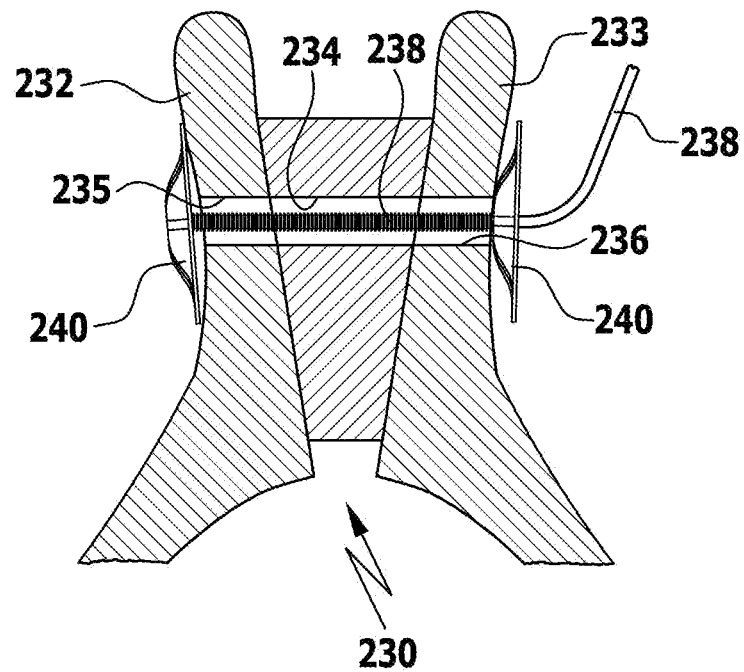
FIGS. 25A and 25B show a seventh embodiment of an implant in accordance with the invention with an associated holding element.

FIG. 25A shows a further variant of an implant 230 in accordance with the invention in the installed situation between the halves 232, 233 of a split spinous process.

Differently from the implant bodies 200 of FIG. 24, the implant body 230 has a bore hole 234 arranged transversely to the longitudinal direction or depth of the implant, which is in alignment with corresponding bore holes 235, 236 or cut-outs in the spinous process 232, 233.

When the implant body 230 is in the installed state in the spinous process 232, 233, a wire segment 238, for example, is then inserted through the bore hole 234 and fixed at its free end to a holding element 240. The second free end of the wire segment 238 is also provided with a holding element 240, as reproduced by way of example in an enlarged representation in a plan view and a side view in FIG. 25B.

The wire segment 238 preferably has a structure which allows the holding elements 240 to be fastened to it in a latching manner without a special tool, so that after insertion of the wire segment 238 and the holding elements 240 fixed thereto, the wire segment 238 can essentially be easily clamped and the holding elements 240 made to bear against the outer surfaces of the spinous process parts 232, 233, so as to secure the implant body 230 in the incision gap.

Figure 26A:
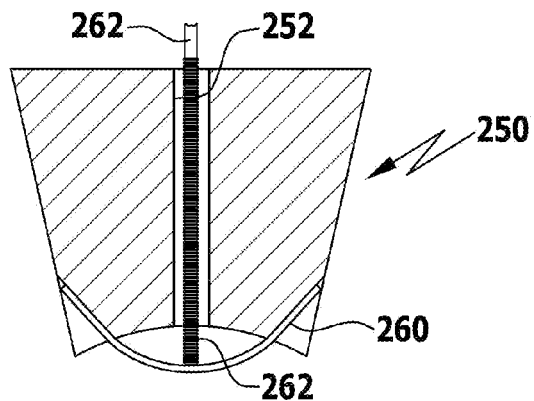
FIGS. 26A to 26C show an eighth embodiment of an implant in accordance with the invention.
Figure 26B:
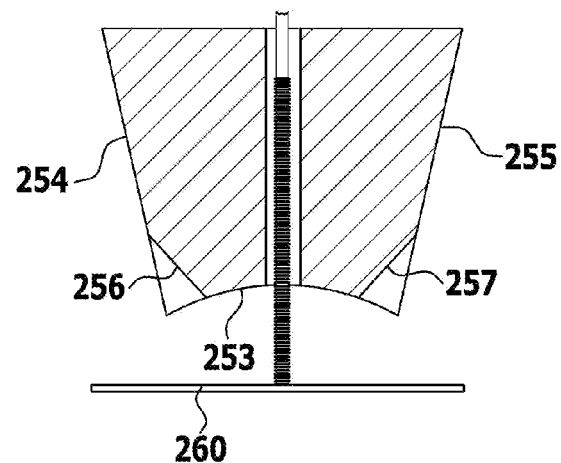
Figure 26C:
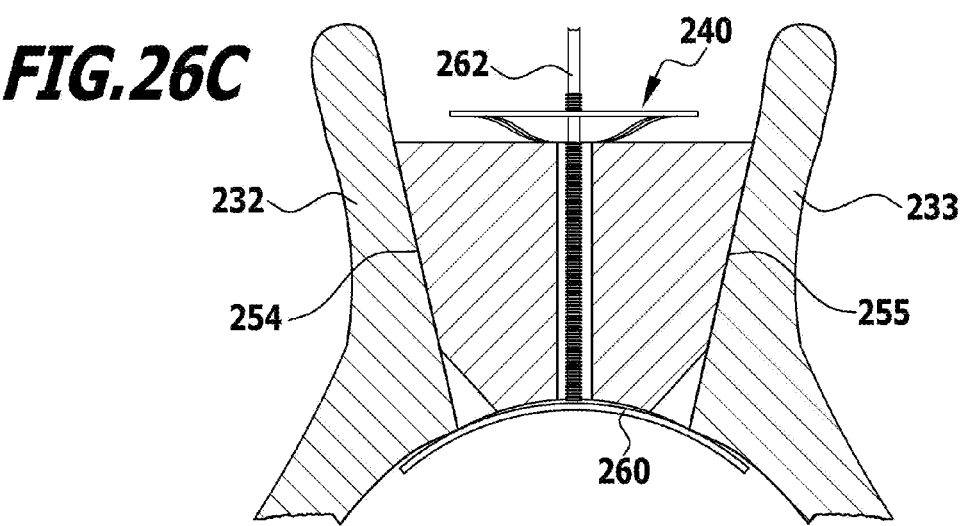

A further variant of an implant in accordance with the invention is shown in illustrations A to C in FIG. 26. Here a further variant for fixing the implant body 250 in its position in the incision gap of a vertebral arch is to be explained.

The implant body 250 has a longitudinal bore hole 252, which leads essentially from the dorsal to the ventral end of the implant 250 and is arranged substantially at the center between the contacting surfaces 254, 255 arranged in the shape of a wedge.

The implant body 250 has at its ventral end next to an indentation 253, already described in the above-mentioned embodiments, recesses 256, 257 adjacent to its contacting or bearing surfaces 254, 255, for enlarging the volume at the spinal canal side.

The implant 250 uses a flat spring element 260, which, for example, may be of strip-shaped configuration, as holding element. A pin 262 which passes through the implant body dorsally is fixed at the center of the holding element 260.

In the state ready for installation, the implant 250 has the holding element 260 in the configuration shown in illustration A of FIG. 26, in which the free ends of the holding element 260 resiliently engage the recesses 256, 257.

In the inserted state of the implant 250, the fixing of the holding element 260 in the recesses 256, 257 is then released via the pin 262, so that the holding element 260 can then unfold and assume a substantially flat configuration, as shown in illustration B of FIG. 26.

Figure 25B:
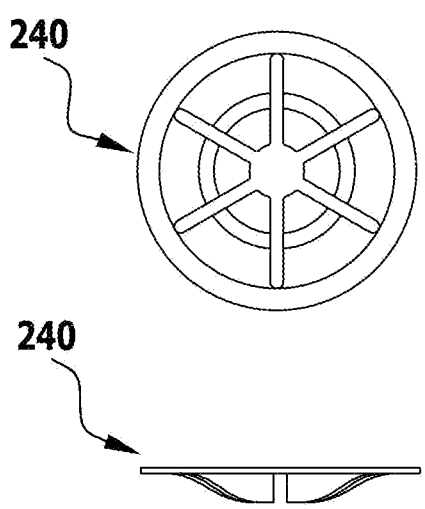

To fix the implant 250 in the incision gap of a vertebral arch, the holding element 260 is then pulled in the dorsal direction and in this position then fixed with a holding element 240, as shown, for example, in FIG. 25B, on the upper side of the implant body 250. The spring type holding element 260 now bears against the inside of the lamina of the vertebra at both sides of the incision gap and against the underside, the ventral side, of the implant 250, and thereby ensures that the implant is fixed in the incision gap of the treated vertebra, as shown in illustration C of FIG. 26.

Figure 27:
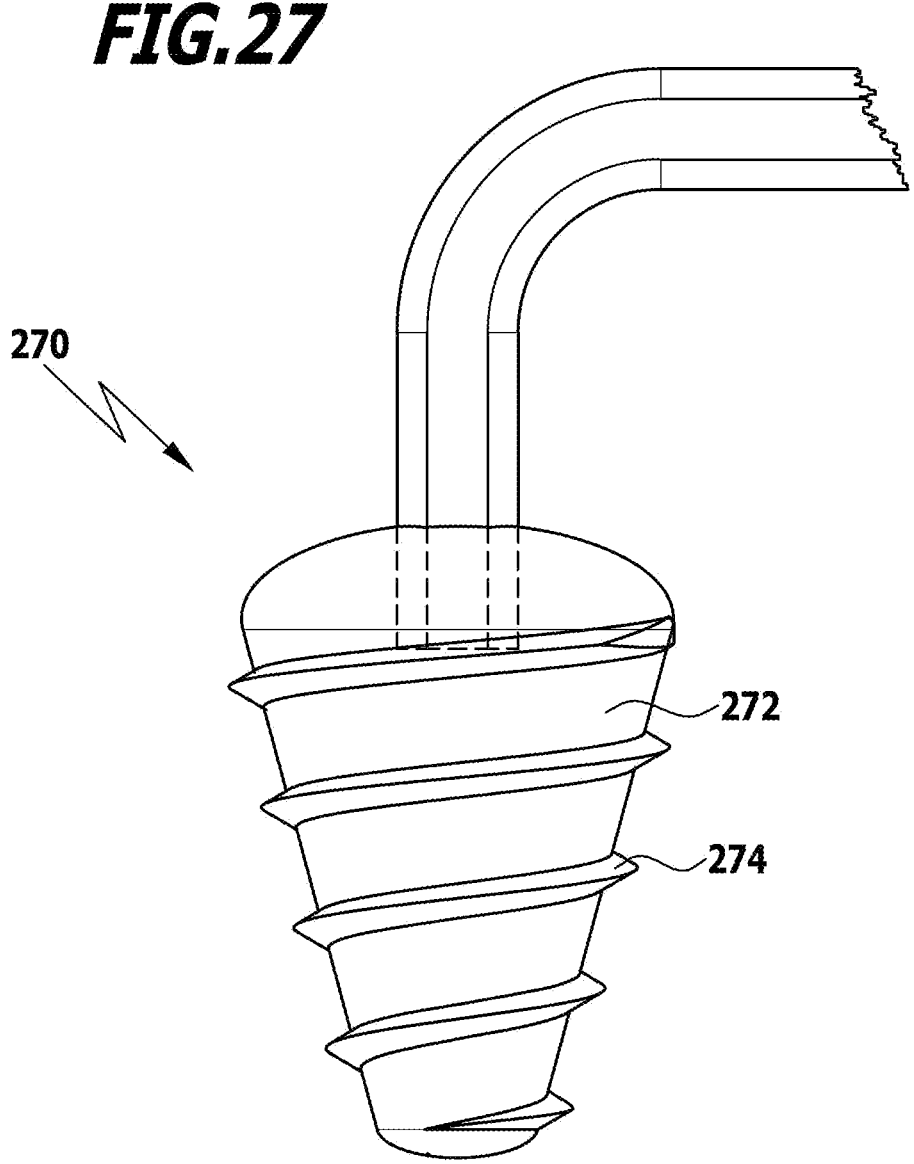
FIG. 27 shows a ninth embodiment of an implant in accordance with the invention.

FIG. 27 shows a further embodiment of an implant 270 in accordance with the invention with a conical implant body 272 which has a screw thread 274 on its outer surface. Differently from the implants described above, the implant 270 does not require any expanded incision gap for insertion. It is advantageous for the incision gap created by splitting the lamina to dorsally comprise opposed recesses in the incision surfaces in which the ventral end area of the implant 270 is first received in a centering manner.

When the implant 270 is subsequently screwed into the incision gap, the thread 274 cuts a counter thread in the bone substance. Owing to the conical shape of the implant body 272, the incision gap is successively expanded during the screwing-in, so that the lamina sections are gradually elastically/plastically deformed.

The conicity of the implant body 272 preferably corresponds to a cone angle of about 5° to about 45°, in particular, of about 7° to about 30°.

What is claimed is:

1. Surgical method for expanding a vertebral canal of a vertebra, comprising:
   a single splitting incision, the single splitting incision splitting a vertebral arch into vertebral arch sections to form an incision gap, the incision gap being bounded by opposed incision surfaces, and
   expanding the incision gap to a prescribed gap width such that the bone substance of the vertebral arch sections is thereby elastically/plastically deformed,
   wherein the expansion of the incision gap, with the bone substance of the vertebral arch sections thereby being elastically/plastically deformed, is performed such that forces acting on the incision surfaces are limited to about 500 N or less, preventing fracturing of lamina of the vertebral arch,
   wherein the single splitting incision is the only incision made in the vertebral arch.

2. Method in accordance with claim 1, wherein the vertebral arch is split in an area of the spinous process.

3. Method in accordance with claim 1, wherein the elastic/plastic deformation is performed without weakening further areas of the vertebral arch.

4. Method in accordance with claim 1, wherein following partial expansion of the incision gap, bone substance of the vertebral arch is removed from a side of the vertebral arch facing the spinal canal, and the incision gap is then fully expanded to the prescribed gap width.

5. Method in accordance with claim 1, wherein the incision gap is expanded to a prescribed gap width of about 5 mm to about 15 mm, measured at an end of the incision gap on a spinal canal side.

6. Method in accordance with claim 1, wherein the expansion is performed at a rate of about 10 seconds to about 60 seconds, per 5 mm enlargement of the incision gap.

7. Method in accordance with claim 1, wherein an implant is inserted into the expanded incision gap and is supported at the incision surfaces of the incision gap.

8. Method in accordance with claim 1, wherein the incision surfaces of the incision gap are each formed with at least one recess.

9. Method in accordance with claim 1, wherein the incision surfaces are substantially flat with the exception of optional areas containing recesses.

10. Method in accordance with claim 7, wherein the implant has projections on opposed surfaces, and the implant is positioned in the incision gap such that the projections engage recesses of the incision surfaces.

11. Method in accordance with claim 10, wherein the implant has a wedge-shaped body, and the projections are arranged on wedge surfaces of the body.

12. Method in accordance with claim 8, wherein the recesses of the incision surfaces are formed as grooves, which are of substantially semi-cylindrical configuration.

13. Method in accordance with claim 12, wherein the grooves are formed so as to extend substantially parallel to a longitudinal direction of the spinous process.

14. Method in accordance with claim 1, wherein the incision gap is expanded with a distraction instrument, said distraction instrument having two working ends which are adapted for engagement with positive locking in recesses of the incision surfaces.

15. Method in accordance with claim 1, wherein the incision gap is expanded with a distraction instrument having at working ends thereof outwardly protruding projections which are positionable on a surface of the vertebral arch sections on a spinal canal side.

16. Method in accordance with claim 14, wherein the working ends of the distraction instrument form a stop for an implant to be inserted into the incision gap.

17. Method in accordance with claim 7, wherein the implant is fixed in the incision gap of the vertebral arch.

18. Method in accordance with claim 17, wherein the implant is fixed with a substance-to-substance bond in the incision gap by means of one of adhesion or welding.

19. Method in accordance with claim 17, wherein the implant is fixed with at least one of force locking and positive locking in the incision gap.

20. Method in accordance with claim 19, wherein the implant is fixed by means of screws or bolts penetrating the incision surfaces of the incision gap.

21. Method in accordance with claim 19, wherein the implant is fixed by means of plastification of a dowel.

22. Method in accordance with claim 19, wherein the implant is fixed in the incision gap by means of holding elements supported at a surface of the vertebral arch sections.

23. Method in accordance with claim 1, wherein a spacer is intermediately inserted into the partially or fully expanded incision gap, said spacer preferably being of U-shaped configuration, and said spacer is optionally replaced by an implant in a subsequent step.

24. Method in accordance with claim 23, wherein the spacer is additionally fixed extracorporeally.

25. Method in accordance with claim 17, wherein the implant has an osteointegrative coating.

* * * * *